(12) United States Patent
Levitz et al.

(10) Patent No.: US 10,753,874 B2
(45) Date of Patent: Aug. 25, 2020

(54) HANDHELD MOBILE DEVICE FOR DETECTION OF BIOLOGICAL EVIDENCE

(71) Applicant: MOBILEODT LTD., Tel Aviv (IL)

(72) Inventors: David Levitz, Tel Aviv (IL); Ariel Beery, Tel Aviv (IL); Ronit Slyper, Tel Aviv (IL)

(73) Assignee: MOBILEODT LTD., Tel Aviv (IL)

( * ) Notice: Subject to any disclaimer, the term of this patent is extended or adjusted under 35 U.S.C. 154(b) by 0 days.

(21) Appl. No.: 15/758,079

(22) PCT Filed: Sep. 7, 2016

(86) PCT No.: PCT/IL2016/050991
§ 371 (c)(1),
(2) Date: Mar. 7, 2018

(87) PCT Pub. No.: WO2017/042807
PCT Pub. Date: Mar. 16, 2017

(65) Prior Publication Data
US 2018/0252647 A1  Sep. 6, 2018

Related U.S. Application Data

(60) Provisional application No. 62/215,074, filed on Sep. 7, 2015.

(51) Int. Cl.
*G01N 21/64* (2006.01)
*G01N 21/21* (2006.01)
(Continued)

(52) U.S. Cl.
CPC ....... *G01N 21/6456* (2013.01); *A61B 5/0077* (2013.01); *G01J 3/0224* (2013.01);
(Continued)

(58) Field of Classification Search
CPC ............... G01N 21/6456; G01N 21/21; G01N 21/4738; G01N 2201/0221; G01J 3/0264;
(Continued)

(56) References Cited

U.S. PATENT DOCUMENTS 5,929,443 A   7/1999  Alfano et al.
6,323,846 B1  11/2001 Westerman et al.
(Continued)

OTHER PUBLICATIONS

Steven L. Jacques et al, "Imaging skin pathology with polarized light", Journal of Biomedical Optics 7(3), 329-340, 2002.
(Continued)

*Primary Examiner* — Twyler L Haskins
*Assistant Examiner* — Angel L Garces-Rivera
(74) *Attorney, Agent, or Firm* — The Roy Gross Law Firm, LLC; Roy Gross

(57) ABSTRACT

A system including: a mobile device, including: a camera configured to capture multiple images of a subject; a processor configured to identify a first image of the captured images as a blue frame, wherein the image was captured while the subject was illuminated by blue light, and identify a second image of one of the captured images as a white frame, wherein the image was captured while the subject was illuminated by white light; associate the blue frame with the white frame; detect a feature depicted in the blue frame that is not depicted in the associated white frame, and indicate the detection of the feature to a user; and a user interface display configured to separately render the blue frame and the white frame.

19 Claims, 15 Drawing Sheets

(51) Int. Cl.
*G06T 7/00* (2017.01)
*G01N 21/47* (2006.01)
*G01J 3/02* (2006.01)
*G01J 3/32* (2006.01)
*G01J 3/10* (2006.01)
*G01J 3/42* (2006.01)
*G01J 3/28* (2006.01)
*A61B 5/00* (2006.01)
*H04N 5/225* (2006.01)
*H04N 5/445* (2011.01)

(52) U.S. Cl.
CPC ........... *G01J 3/0237* (2013.01); *G01J 3/0264* (2013.01); *G01J 3/0272* (2013.01); *G01J 3/0283* (2013.01); *G01J 3/10* (2013.01); *G01J 3/2823* (2013.01); *G01J 3/32* (2013.01); *G01J 3/42* (2013.01); *G01N 21/21* (2013.01); *G01N 21/4738* (2013.01); *G06T 7/0014* (2013.01); *H04N 5/2256* (2013.01); *H04N 5/44504* (2013.01); *H04N 5/44591* (2013.01); *G01J 2003/102* (2013.01); *G01J 2003/2826* (2013.01); *G01N 2201/0221* (2013.01); *G06T 2200/24* (2013.01); *G06T 2207/10064* (2013.01); *G06T 2207/10152* (2013.01)

(58) Field of Classification Search
CPC ...... G01J 3/0272; G01J 3/0224; G01J 3/0237; G01J 3/42; G01J 3/32; G01J 3/2823; G01J 3/10; G01J 3/0283; G01J 2003/102; G01J 2003/2826; H04N 5/2256; H04N 5/44591; H04N 5/44504; G06T 7/0014; G06T 2207/10152; G06T 2207/10064; G06T 2200/24
See application file for complete search history.

(56) References Cited

U.S. PATENT DOCUMENTS

| | | | |
|---|---|---|---|
| 6,570,557 B1 | 5/2003 | Westerman et al. |
| 6,677,932 B1 | 1/2004 | Westerman et al. |
| 7,477,767 B2 | 1/2009 | Chhibber et al. |
| 7,614,008 B2 | 11/2009 | Ording |
| 7,633,076 B2 | 12/2009 | Huppi et al. |
| 7,653,883 B2 | 1/2010 | Hotelling et al. |
| 7,663,607 B2 | 2/2010 | Otelling et al. |
| 7,844,914 B2 | 11/2010 | Andre et al. |
| 7,957,762 B2 | 6/2011 | Herz et al. |
| 8,006,002 B2 | 8/2011 | Kalayjian et al. |
| 8,239,784 B2 | 8/2012 | Hotelling et al. |
| 8,279,180 B2 | 10/2012 | Hotelling et al. |
| 8,381,135 B2 | 2/2013 | Hotelling et al. |
| 8,479,122 B2 | 7/2013 | Hotelling et al. |
| 9,348,458 B2 | 5/2016 | Hotelling et al. |
| 2002/0055024 A1 | 5/2002 | Lee et al. |
| 2004/0125996 A1 | 7/2004 | Eddowes et al. |
| 2005/0190059 A1 | 9/2005 | Wehrenberg |
| 2006/0017692 A1 | 1/2006 | Wehrenberg et al. |
| 2007/0064979 A1 | 3/2007 | Chhibber et al. |
| 2007/0150842 A1 | 6/2007 | Chaudhri et al. |
| 2007/0171210 A1 | 7/2007 | Chaudhri et al. |
| 2010/0165089 A1 | 7/2010 | Liang et al. |
| 2012/0194665 A1 | 8/2012 | Kilian et al. |
| 2013/0300850 A1 | 11/2013 | Millikan |
| 2015/0212074 A1 | 7/2015 | Xiang et al. |
| 2016/0070399 A1 | 3/2016 | Hotelling |
| 2016/0084751 A1 | 3/2016 | Levitz et al. |

OTHER PUBLICATIONS

Steven L. Jacques et al, "Rapid spectral analysis for spectral imaging", Biomedical Optics Express 157, vol. 1, No. 1, 2010.
International Search Report PCT/IL2016/050991 Completed Dec. 20, 2016; dated Jan. 3, 2017 4 pages.
Written Opinion of the International Searching Authority PCT/IL2016/050991 dated Jan. 2, 2017 6 pages.
Zhu et al., "Cost-effective and compact wide-field fluorescent imaging on a cell-phone", The Royal Society of Chemistry, Jan. 21, 2011; 11(2), 315-322.
Blanco et al., "Fluorescence Diagnosis of Upper Respiratory Tract Infections", Proc. of SPIE vol. 9531, 953137-1-6, Jun. 19, 2015.
Intaravanne et al., "Ripeness Level Indication of Bananas with Visible and Fluorescent Spectral Images", IEEE, pp. 1-4, May 2012.
Intaravanne et al., "Cell phone-based two-dimensional spectral analysis for banana ripeness estimation", Elsevier, Sensors and Actuators B: Chemical; vol. 168 (Jun. 20, 2012), pp. 390-394.
Mayinger et al., "Fluorescence induced with 5-aminolevulinic acid for the endoscopic detection and follow-up of esophageal lesions", Gastrointestinal Endoscopy, Nov. 2001; 54(5): 572-8.

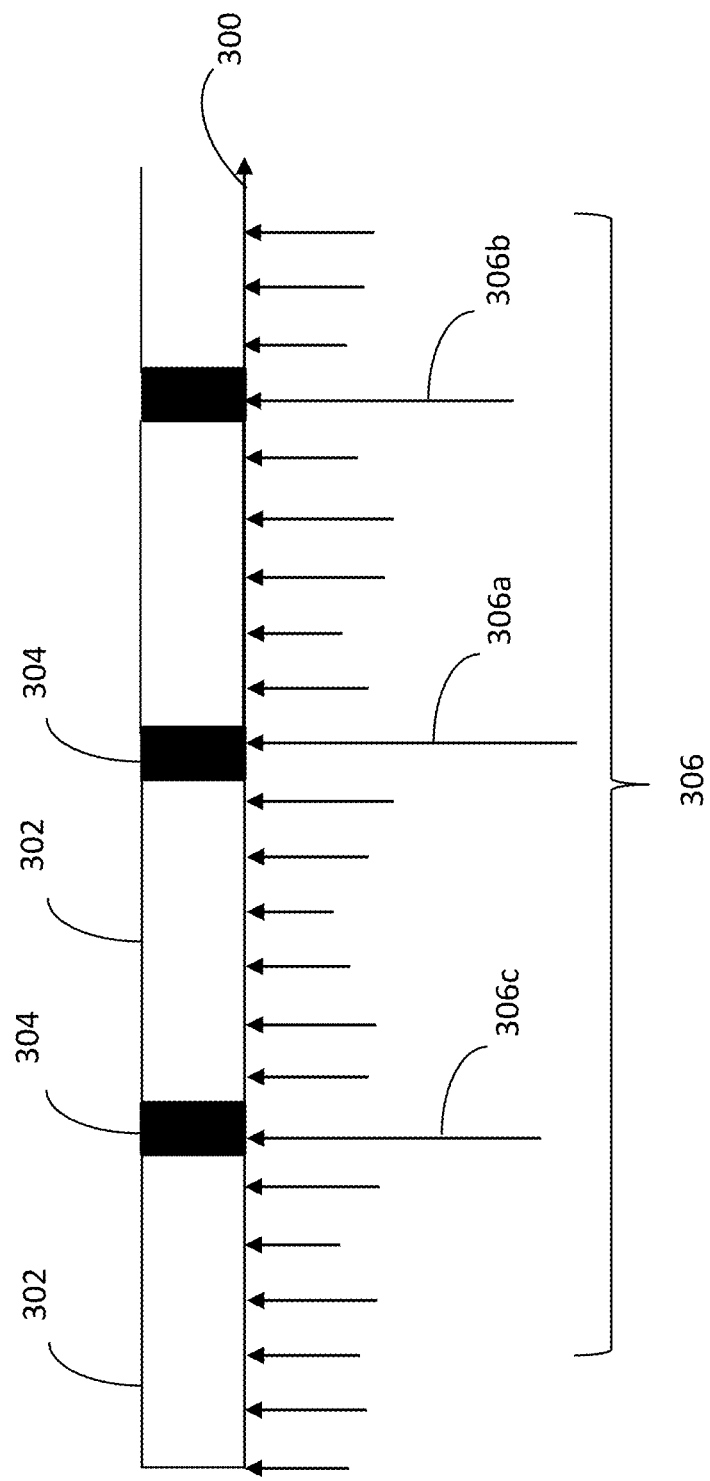

HANDHELD MOBILE DEVICE FOR DETECTION OF BIOLOGICAL EVIDENCE

CROSS-REFERENCE TO RELATED PATENT APPLICATIONS

This application is a national phase of PCT Patent Application No. PCT/IL2016/050991 having International filing date of Sep. 7, 2016, which claims the benefit of priority of U.S. Provisional Patent Application No. 62/215,074, filed Sep. 7, 2015 and entitled "Handheld Mobile Device for Detection of Biological Evidence". The contents of the above applications are all incorporated by reference as if fully set forth herein in their entirety.

FIELD OF THE INVENTION

The invention relates to the field of handheld mobile devices.

BACKGROUND

Ultraviolet (UV) light is commonly used to detect fluorescing substances that may be invisible to the human eye under regular visible light. Detecting fluorescing bodily substances, such as blood, semen, saliva, or urine on victims of assault, typically requires costly equipment to illuminate areas of the victim's body with a special UV lamp, and record the images with a special camera configured with a special lens. In developing counties, the cost of such equipment can be prohibitive, preventing diagnosis and subsequent treatment of victims, particularly in rural areas that have no access to a health facility that can accommodate such expensive equipment.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a system comprising: a multifunction mobile device, comprising: a camera configured to capture multiple frames of a subject; a processor configured to identify a first frame of the multiple captured frames as a blue frame, wherein the first frame was captured while the subject was illuminated by blue light, identify a second frame of the multiple captured frames as a white frame, wherein the second frame was captured while the subject was illuminated by white light; associate the blue frame with the white frame; detect a feature depicted in the blue frame that is not depicted in the associated white frame, indicate the detection of the feature to a user; and a user interface display configured to separately render the blue frame and the white frame.

In some embodiments, the processor is further configured to determine a peak blue level of the captured frames.

In some embodiments, identifying the blue frame and identifying the white frame comprises synchronizing the identification of the frames with a predefined alternating blue light and white light illumination cycle using a time stamp associated with the captured frames, and a time stamp associated with the peak blue level.

In some embodiments, the feature is associated with a fluorescing substance.

In some embodiments, the white frame is rendered on a primary portion of the user interface and wherein the blue frame is rendered, simultaneous to rendering the white frame, on a secondary portion of the user interface.

In some embodiments, responsive to an indication by a user, the blue frame is rendered on a combination of the primary and secondary portions of the display.

In some embodiments, responsive to an indication by a user, the blue frame is rendered on the primary portion of the display, and, simultaneous to rendering the blue frame, the white frame is rendered on the secondary portion of the display.

In some embodiments, the system further comprises a mount configured to enable supporting the multifunction mobile device with a user's finger, thereby freeing the user's thumb to interact with the user interface.

In some embodiments, indicating the detection of the feature comprises at least one of: sounding an alert, causing the device to vibrate, or flashing a signal.

In some embodiments, indicating the detection of the feature comprises displaying a graphic indicator overlayed on the rendering of the white frame at a location corresponding to the location of the detected feature on the associated blue frame.

In some embodiments, displaying the graphic indicator comprises any of:
  a) displaying an outline around the feature,
  b) displaying a box surrounding the feature, displaying an arrow pointing to the feature,
  c) simultaneously displaying the white frame in association with a scaled-down rendering of the blue frame,
  d) displaying a partially transparent rendition of the blue frame overlaid on the associated white frame,
  e) displaying a zoomed view of the detected feature,
  f) displaying a corresponding portion of the blue frame overlayed on the displayed white frame responsive to an indication by the user,
  g) displaying any of the graphic indicators of a) to f) in a pulsed manner,
  h) displaying a meter indicating a level of interest for the detected feature.

In some embodiments, rendering the blue frame separately from the white frame comprises alternately rendering the blue frame and white frame on a common portion of the display.

In some embodiments, the system further comprises a lamp configured to alternately emit white light and blue light at a predefined illumination cycle.

In some embodiments, the lamp is mounted with the multifunction mobile device.

In some embodiments, the lamp is provided with a shield to block the blue and white light from illuminating a line of sight of a user.

In some embodiments, the processor is further configured to store the blue frame in association with the white frame.

In some embodiments, the processor is further configured to store an audio file in association with the blue frame and white frame.

In some embodiments, the system further comprises a polarization difference imaging (PDI) acquisition apparatus configured to acquire a PDI image of the subject, wherein the processor is further configured to detect a PDI feature depicted in the PDI image that is not depicted in any of the blue frame and the white frame, and indicate the detection of the PDI feature There is provided, in accordance with an embodiment, a computer program product comprising a non-transitory computer-readable storage medium having program code embodied therewith, the program code executable by at least one hardware processor to: identify a first frame of multiple captured frames of a subject as a blue frame, wherein the first frame was captured while the subject was illuminated by blue light, identify a second frame of the multiple captured frames of the subject as a white frame, wherein the second frame was captured while the subject was illuminated by white light, and associate the blue frame with the white frame; detect a feature depicted in the blue frame that is not depicted in the associated white frame; and separately render the blue frame and the white frame on a user interface display, and indicate the detection of the feature to a user.

In some embodiments, identifying the blue frame and the identifying the white frame comprises determining a peak blue level of the captured frames.

In some embodiments, the program code is further executable to synchronize the identification of the blue and white frames to a predefined alternating blue light and white light illumination cycle using a time stamp associated with the blue and white frames, and a time stamp of the peak blue level.

In some embodiments, the feature is associated with a fluorescing substance.

In some embodiments, separately rendering comprises simultaneously rendering the white frame on a primary portion of the user interface display and rendering the blue frame on a secondary portion of the user interface display.

In some embodiments responsive to an indication by a user, the program code is further executable to render the blue frame on a combination of the primary and secondary portions of the user interface display.

In some embodiments, responsive to an indication by a user, the program code is further executable to simultaneously render the blue frame on the primary portion of the user interface display, and render the white frame on the secondary portion of the user interface display.

In some embodiments indicating the detection of the feature comprises performing at least one of: sounding an alert, causing the device to vibrate, or flashing a signal.

In some embodiments, indicating the detection of the feature comprises displaying a graphic indicator overlaid on the rendering of the white frame at a location corresponding to the location of the detected feature on the associated blue frame.

In some embodiments, displaying the graphic indicator comprises any of:
  a) displaying an outline around the feature,
  b) displaying a box surrounding the feature, displaying an arrow pointing to the feature,
  c) simultaneously displaying the white frame in association with a scaled-down rendering of the blue frame,
  d) displaying a partially transparent rendition of the blue frame overlaid on the white frame,
  e) displaying a zoomed view of the detected feature,
  f) displaying a corresponding portion of the blue frame overlayed on the displayed white frame responsive to an indication by the user,
  g) displaying any of the graphic indicators of a) to f) in a pulsed manner,
  h) displaying a meter indicating a level of interest for the detected feature.

In some embodiments, rendering the blue frame separately from the white frame comprises alternately rendering the blue frames and white frames on a common portion of the display.

In some embodiments, the program code is further executable to store the blue frame in association with the white frame.

In some embodiments, the program code is further executable to store an audio file in association with the blue frame and associated white frame.

In some embodiments, the program code is further executable to receive a polarization difference imaging (PDI) image of the subject, detecting a PDI feature depicted in the PDI image that is not depicted in any of the blue frame and the white frame, and indicating the detection of the PDI feature.

There is provided, in accordance with an embodiment, a method, comprising: capturing multiple frames of a subject; identifying a first frame of the multiple captured frames as a blue frame, wherein the first frame was captured while the subject was illuminated by blue light; identifying a second frame of the multiple captured frames as a white frame, wherein the second image was captured while the subject was illuminated by white light; associating the blue frame with the white frame; detecting a feature depicted in the blue frame that is not depicted in the associated white frame; separately rendering the blue frame and the white frame on a user interface display; and indicating the detection of the feature to a user.

In some embodiments, the method further comprises determining a peak blue level of the captured frames.

In some embodiments, identifying the blue frame and identifying the white frame comprises synchronizing the identification of the frames with a predefined alternating blue light and white light illumination cycle using a time stamp associated with the captured frames and a time stamp associated with the peak blue level.

In some embodiments, the feature is associated with a fluorescing substance.

In some embodiments, separately rendering comprises rendering the white frame on a primary portion of the user interface display and simultaneously rendering the blue frame on a secondary portion of the user interface display.

In some embodiments, responsive to an indication by a user, rendering the blue frame on a combination of the primary and secondary portions of the user interface display.

In some embodiments, responsive to an indication by a user, simultaneously rendering the blue frame on the primary portion of the user interface display, and rendering the white frame on the secondary portion of the user interface display.

In some embodiments, indicating the detection of the feature comprises performing at least one of: sounding an alert, causing the device to vibrate, or flashing a signal.

In some embodiments, indicating the detection of the feature comprises displaying a graphic indicator overlayed on the rendering of the white frame at a location corresponding to the location of the detected feature on the associated blue frame.

In some embodiments, displaying the graphic indicator comprises any of:
  a. displaying an outline around the feature,
  b. displaying a box surrounding the feature, displaying an arrow pointing to the feature,
  c. simultaneously displaying the white frame in association with a scaled-down rendering of the blue frame, d. displaying a partially transparent rendition of the blue frame overlaid on the associated white frame,
e. displaying a zoomed view of the detected feature,
f. displaying a corresponding portion of the blue frame overlayed on the displayed white frame responsive to an indication by the user,
g. displaying any of the graphic indicators of a) to f) in a pulsed manner,
h. displaying a meter indicating a level of interest for the detected feature.

In some embodiments, rendering the blue frame separately from the white frame comprises alternately rendering the blue frame and white frame on a common portion of the display.

In some embodiments, the method further comprises storing the identified blue frame in association with the associated identified white frame.

In some embodiments, the method further comprises storing an audio file in association with the blue frame and associated white frame.

In some embodiments, the method is further executable to receive a polarization difference imaging (PDI) image of the subject, detecting a PDI feature depicted in the PDI image that is not depicted in any of the blue frame and the white frame, and indicating the detection of the PDI feature.

There is provided, in accordance with an embodiment, a system comprising: a multifunction mobile device, comprising: a camera configured to capture multiple frames of a subject; a processor configured to identify one or more multi-spectral frames of the multiple captured frames, wherein the one or more multi-spectral frames was captured while the subject was illuminated by multi-spectral light, identify a white frame of the multiple captured frames, wherein the white frame was captured while the subject was illuminated by white light; associate the one or more multi-spectral frames with the white frame; detect a feature depicted in the one or more multi-spectral frames that is not depicted in the associated white frame, indicate the detection of the feature to a user; and a user interface display configured to separately render the one or more multi-spectral frames and the white frame.

In some embodiments, the multi-spectral light has a wavelength selected from a group consisting of: blue light; ultra-violet light; approximately 414 nanometers (nm), approximately 542 nm, and approximately 576 nm, corresponding to peak absorption spectra for oxy-hemoglobin ($HbO_2$); approximately 432 nm and approximately 556 nm, corresponding to peak absorption spectra for deoxy-hemoglobin (Hb); approximately 438 nm, approximately 464 nm, and approximately 654 nm, corresponding to a peak difference in absorption between $HbO_2$ and Hb; approximately 259.9 nm, approximately 339.5 nm, approximately 390.0 nm, approximately 422.0 nm, approximately 452.3 nm, approximately 500.1 nm, approximately 529.2 nm, approximately 545.2 nm, approximately 570.1 nm, approximately 584.0 nm, approximately 796.8 nm, corresponding to isobestic points for the absorption spectra of $HbO_2$ and Hb; approximately 970 nm corresponding to a peak absorption level for water; a reference wavelength ranging between approximately 450-550 nm, corresponding to a scattering spectra; a wavelength below the reference wavelength corresponding to Rayleigh scattering; and a wavelength above the reference wavelength corresponding to Mie scattering.

In some embodiments, the processor is further configured to determine one or more peak multi-spectral levels of the captured frames.

In some embodiments, identifying the one or more multi-spectral frames and identifying the white frame comprises synchronizing the identification of the frames with a pre-defined illumination cycle of alternating multi-spectral wavelengths, and white light using a time stamp associated with the captured frames, and a time stamp associated with the peak multi-spectral levels.

In some embodiments, the feature is associated with a substance selected from the group consisting of: a fluorescing substance, water, oxy-hemoglobin ($HbO_2$), and deoxy-hemoglobin (Hb) collagen fibrils, cytoskeletal proteins, nuclei and mitochondria.

In some embodiments, the white frame is rendered on a primary portion of the user interface and wherein any of the multi-spectral frames are rendered, simultaneous to rendering the white frame, on a secondary portion of the user interface.

In some embodiments, responsive to an indication by a user, the multi-spectral frames are rendered on a combination of the primary and secondary portions of the display.

In some embodiments, responsive to an indication by a user, the multi-spectral frames are rendered on the primary portion of the display, and, simultaneous to rendering the multi-spectral frames, the white frame is rendered on the secondary portion of the display.

In some embodiments, indicating the detection of the feature comprises at least one of: sounding an alert, causing the device to vibrate, or flashing a signal.

In some embodiments, indicating the detection of the feature comprises displaying a graphic indicator overlaid on the rendering of the white frame at a location corresponding to the location of the detected feature on the associated multi-spectral frame.

In some embodiments, displaying the graphic indicator comprises any of:
i) displaying an outline around the feature,
j) displaying a box surrounding the feature, displaying an arrow pointing to the feature,
k) simultaneously displaying the white frame in association with a scaled-down rendering of the multi-spectral frame,
l) displaying a partially transparent rendition of the multi-spectral frame overlaid on the associated white frame,
m) displaying a zoomed view of the detected feature,
n) displaying a corresponding portion of the multi-spectral frame overlaid on the displayed white frame responsive to an indication by the user,
o) displaying any of the graphic indicators of a) to f) in a pulsed manner,
p) displaying a meter indicating a level of interest for the detected feature.

In some embodiments, rendering the multi-spectral frame separately from the white frame comprises alternately rendering the multi-spectral frame and white frame on a common portion of the display.

In some embodiments, the system further comprises a lamp configured to alternately emit white light and multi-spectral light at a predefined illumination cycle.

In some embodiments, the lamp is mounted with the multifunction mobile device.

In some embodiments, the processor is further configured to store the multi-spectral frames in association with the white frame.

In some embodiments, the processor is further configured to store an audio file in association with the multi-spectral frames and white frame.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 3A-3B illustrate a schematic diagram for synchronizing the rendering of blue and white frames with an illumination cycle;

DETAILED DESCRIPTION

A system and method are disclosed herein to detect fluorescing substances using a standard handheld mobile device, such as a cellular phone. A subject may be illuminated using a light source alternately emitting white light and ultraviolet (UV) and/or blue light source (hereinafter 'blue' light). Multiple images of the subject thus illuminated may be captured via a camera provided with the device, and may be rendered separately, allowing a user to view the subject illuminated under both white light and/or blue light to discern a feature that is visible only under blue light, thereby identifying the presence of a fluorescing substance on the subject. Additionally, image processing may be performed on the images to detect the feature and alert the user.

Figure 1A:
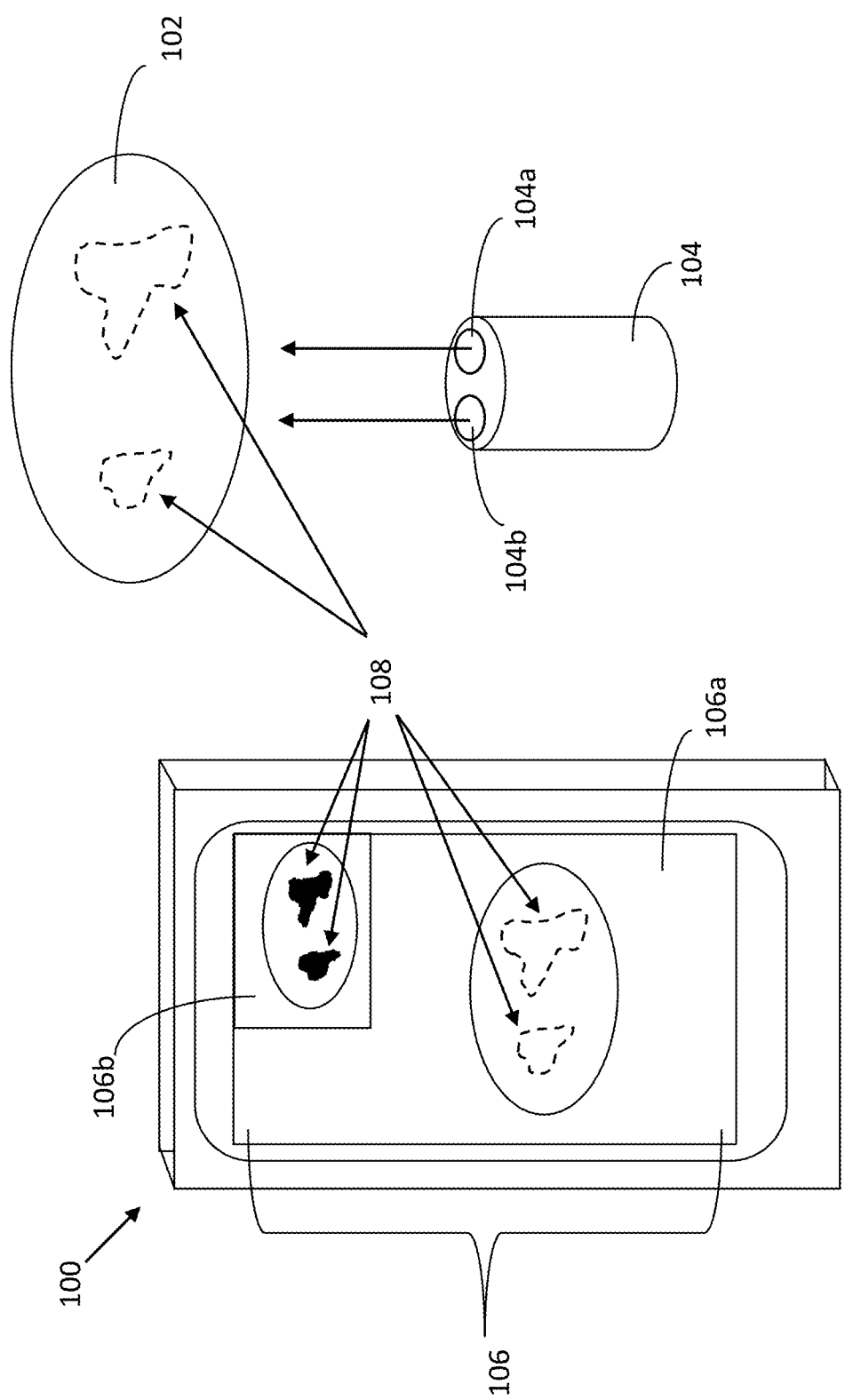
FIGS. 1A-1D illustrate a system for detecting a biological substance using a portable multifunction device, in accordance with an embodiment.

Reference is now made to FIG. 1A which illustrates a simplified conceptual illustration of a system for detecting a feature fluorescing substance using a handheld mobile device, constructed and operative in accordance with an embodiment. A mobile device 100 may be provided with a camera (not shown), such as any standard camera provided with a typical mobile device, to capture multiple images, or frames, of a subject 102 illuminated via a lamp 104. Lamp 104 may illuminate subject 102 with alternately emitted pulses of white light from a white light source 104a and blue and/or UV light (hereinafter 'blue light') from a blue light source 104b. In one embodiment, lamp 104 emits a white and blue light in a cycle comprising of 0.9 seconds of white light followed by for 0.1 seconds of blue light.

Lamp 104 may operate independently of the mobile device, and may be optionally attached to the device using a suitable mount or clip.

Device 100 may be configured to differentiate the frames that are captured while the subject is illuminated by blue light, hereinafter 'blue frames', from the frames that while the subject is illuminated by white light, hereinafter 'white frames', as described in greater detail hereinbelow, and render them separately for viewing by a user.

One or more white frames may be rendered on a primary portion 106a of a display 106 of device 100, and one or more blue frames may be rendered at a secondary portion 100b of display 106. In one embodiment, primary portion 106a comprises the main portion of display 106 and secondary portion 100b comprises a corner of display 106, thereby simultaneously rendering the one or more blue frames and the one or more white frames. Thus, the user may simultaneously observe two views of subject 102: a first view such as may be seen under regular white light illumination without a visible indication of a fluorescing feature, as shown by the dashed lines 108 in display portion 106a, and a second view as seen under illumination by blue light, visibly indicating fluorescing features 108 on subject 102, as shown by the darkened shapes in corner display portion 106b.

Figure 1C:
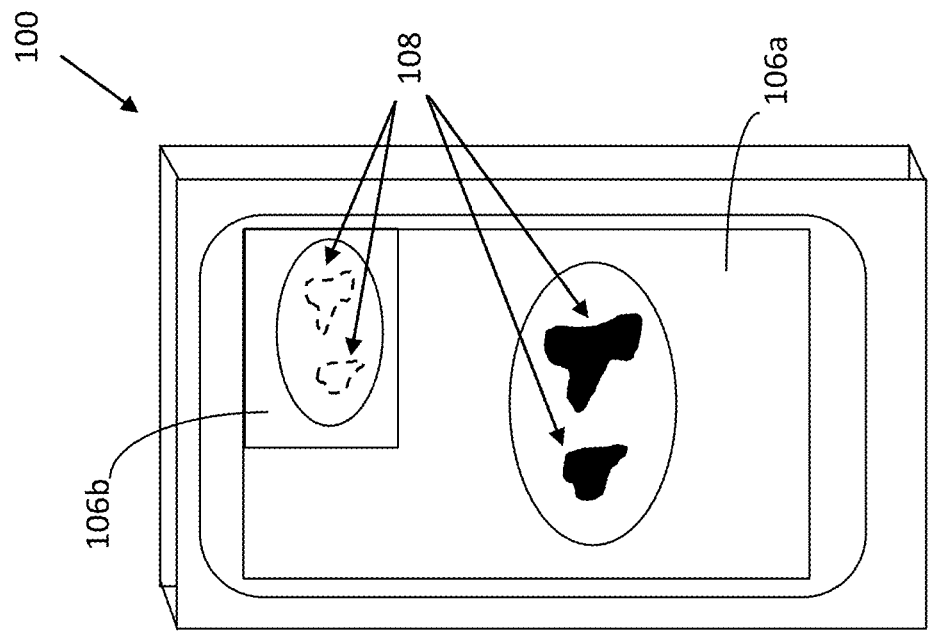
Figure 1B:
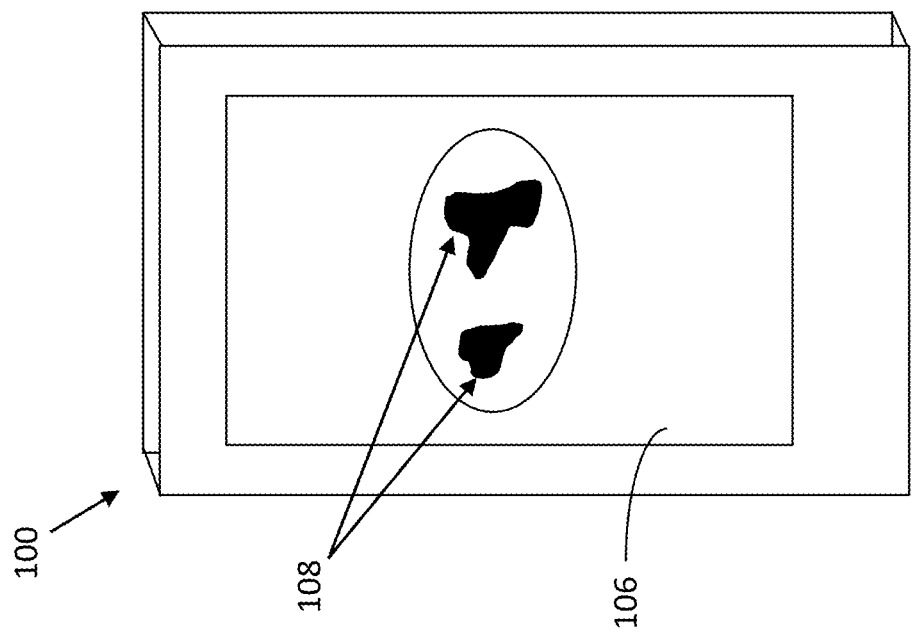

Referring to FIGS. 1B-1C, responsive to an indication by the user, such as detecting a 'touch' on a touch sensitive screen provided with device 100, the blue frames may be rendered on all of display 106 (FIG. 1B) comprising the combination of portions 106a and 106b. Alternatively, the blue frames may be rendered on main display portion 106a and the white frames may be rendered on corner display portion 106b (FIG. 1C), reversing the display described above.

Figure 1D:
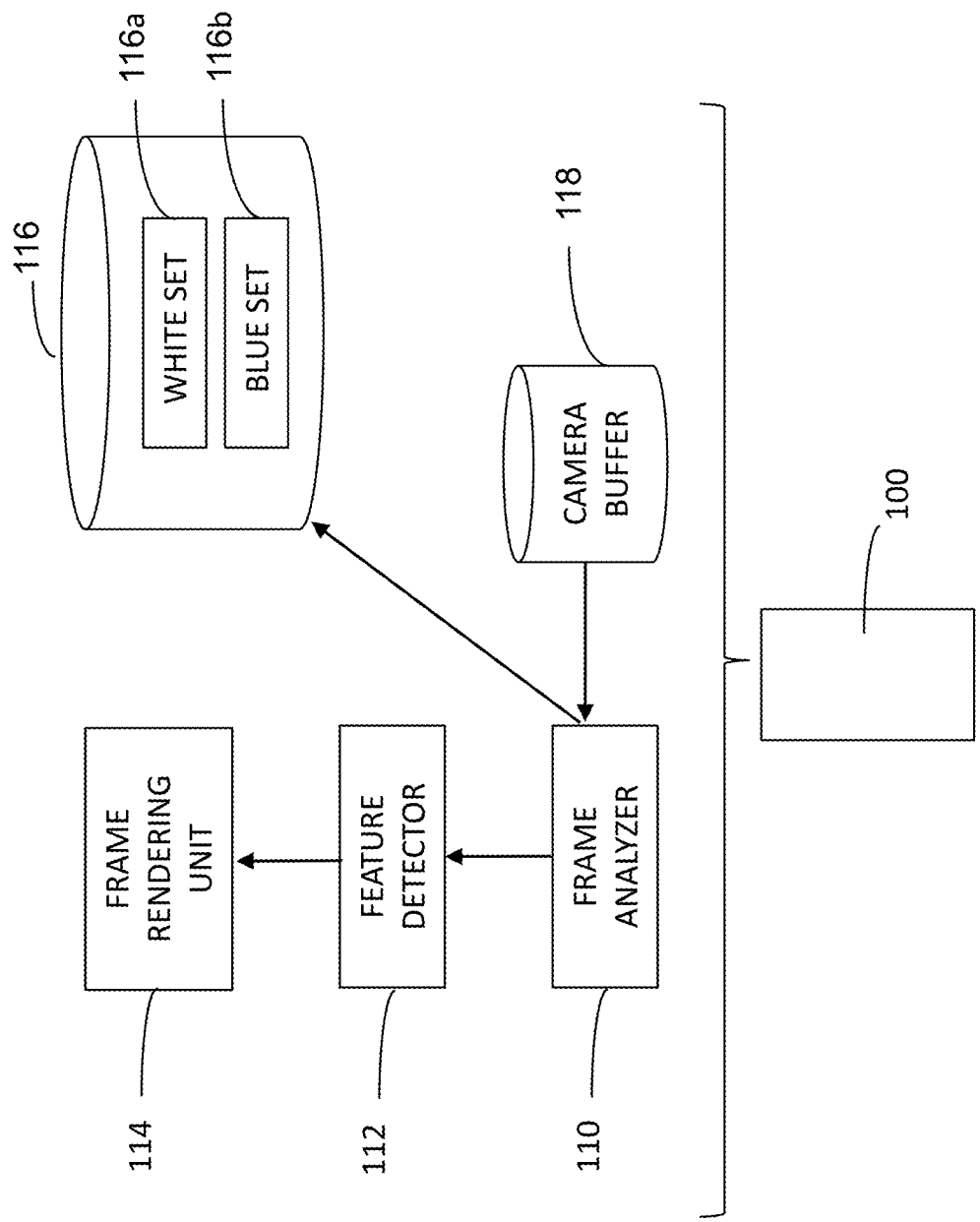

Reference is now made to FIG. 1D which illustrates another view of the systems of FIG. 1A-1C, constructed and operative in accordance with an embodiment. In the system of FIG. 1D, device 100 may be configured with a processor (not shown) configured to implement a frame analyzer 110 that may analyze multiple captured frames stored in a buffer 118 to distinguish between blue frames captured under illumination by blue light, and white frames captured under illumination by white light. In one embodiment, frame analyzer 110 differentiates between the frames by comparing a time stamp associated with the captured image to a predefined illumination cycle.

The processor may implement a feature detector 112 that may detect a feature that is visible only under blue light, such as fluorescing traces of an organic substance like blood or semen that may not be visible under illumination by white light, but may be visible under illumination by blue light. Feature detector 112 may identify the fluorescing feature using any suitable image processing or feature extraction technique. For example, feature detector 112 may compare sequentially captured incoming frames, and detect a feature present in the blue frames that is not present in subsequent or preceding white frames. Feature detector 112 may indicate to the user that a fluorescing feature was detected using any suitable method, such as by sounding an alert, causing the device to vibrate, or flashing a signal, to name a few.

The processor may implement a rendering unit 114 that separately renders the white frames and the blue frames on display 106 of device 100 in accordance with one or more settings, and may highlight the detected feature for discernment by the user.

In one embodiment, the captured frames may be stored in a storage device 116, such as responsive to setting the camera to a 'save image' and/or 'record' setting. The blue frames may be stored in a blue frame set 116a and the white frames may be stored in a white frame set 116b, thereby allowing the user to subsequently view the blue frame set and/or the white frame set. Blue frame set 116a may be associated to white frame set 116b via one or more attributes, or tags, such as a time stamp, a user entered label, or the result of an applied image processing method indicating the association of the frames, to name a few.

In one embodiment, responsive to a user indication to save an image, a white frame may be stored in association with a blue frame, where the respective time stamps of the white and blue frames indicate they were captured within a predefined time duration, such as sequentially. In another embodiment, an audio stream may be recorded while recording a sequence of images. For example, the user may dictate and record details relevant to the condition of the subject. The recording may be stored in storage device 116 in association with the captured images. Frame rendering unit 114 may render the blue frame set 116a and/or the white frame set 116b at a modified frame rate to allow for a non-distorted simultaneous rendering of the corresponding audio recording, accordingly.

A mount (not shown) may be provided to allow a user to support device 100 with a finger, thereby freeing the thumb to swipe the touch-sensitive screen, or otherwise interact with the user interface. Additionally, the mount may optionally support lamp 104, allowing the user to illuminate the subject and operate device 100 with one hand. In an embodiment, the mount may provide a shield that blocks the flashing blue and white light emitted from lamp 104 from the user's line of sight, and focus the emitted light on the subject.

Reference is now made to FIGS. 2A-2J, which illustrate various embodiments for displaying the white and blue frames captured using the system of FIGS. 1A-1D to indicate a detected fluorescing feature. The examples of FIGS. 2A-2J illustrate several exemplary methods to indicate the detection of the feature, and are not meant to be exhaustive. It is to be understood that any suitable method to indicate the detected feature may be used.

Figure 2A:
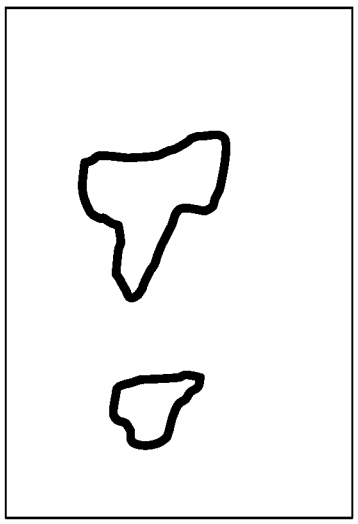
FIGS. 2A-2J illustrate various embodiments for rendering frames of a subject alternately illuminated by blue light and white light.
Figure 2B:
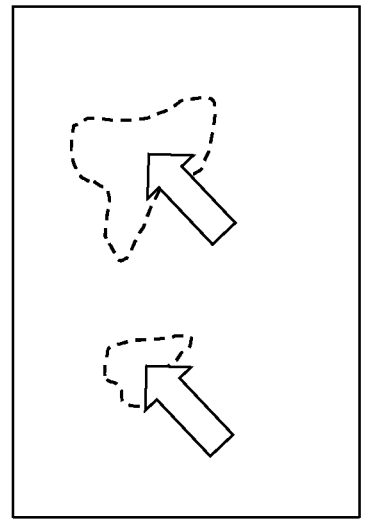
Figure 2C:
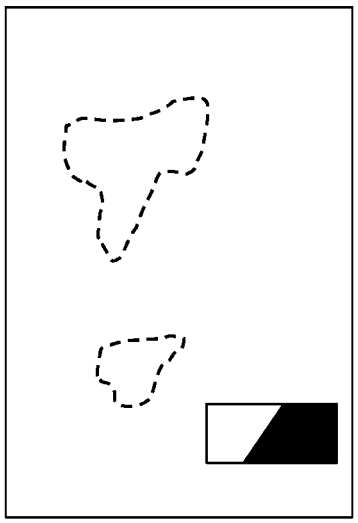
Figure 2D:
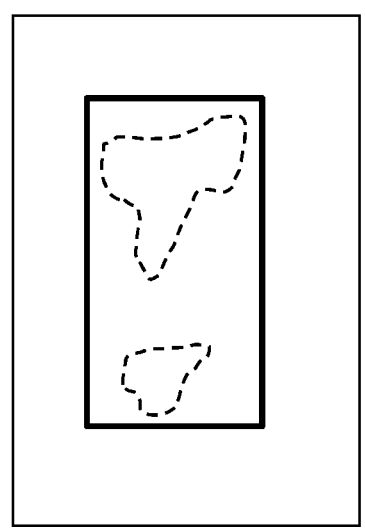
Figure 2F:
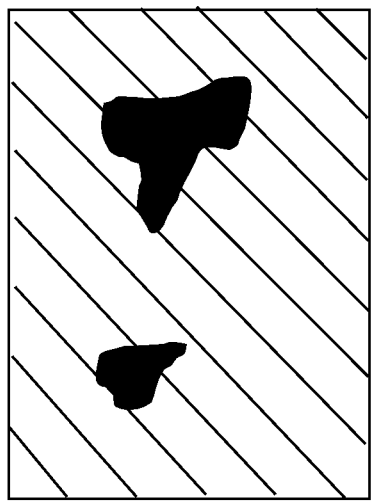
Figure 2H:
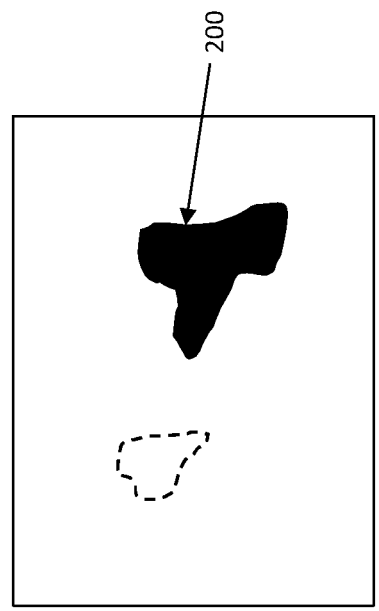
Figure 2E:
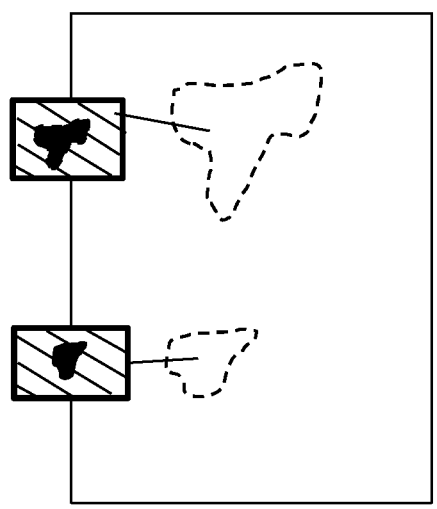
Figure 2G:
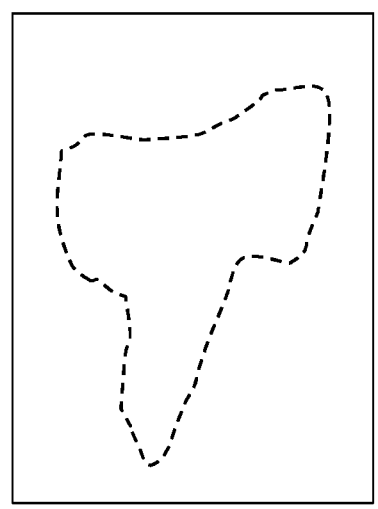

The display of the white frames may include the additionally display of one or more graphic indicators overlaid on or near the detected feature to indicate it to the user, such as may include any combination of the following:
  a meter may be displayed to indicate a level of interest of the viewing region. The level may correspond to an attribute, such as the relative size, intensity, or location of the detected feature (FIG. 2A),
  an outline may be drawn around the feature (FIG. 2B),
  a box may be drawn surrounding the features (FIG. 2C),
  one or more arrows may be displayed to indicate the position of the features (FIG. 2D),
  a scaled-down rendering of the blue frames corresponding to a white frame may be displayed as one or more associated insets (FIG. 2E),
  a partially transparent rendition of the blue frame may be overlaid on the white frame (FIG. 2F),
  upon detecting a feature, the display may automatically zoom into the viewing area including the feature (FIG. 2G),
  responsive to an indication by the user, such as by having the user touch a portion of the touch-sensitive screen, as indicated by an arrow 200, an equivalent portion of the corresponding blue frame may be displayed, overlaid on the white frame (FIG. 2H).

Figure 2I:
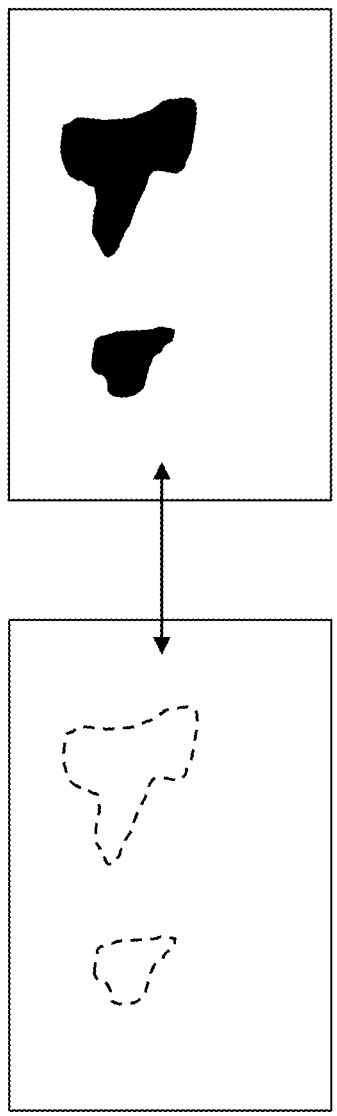
Figure 2J:
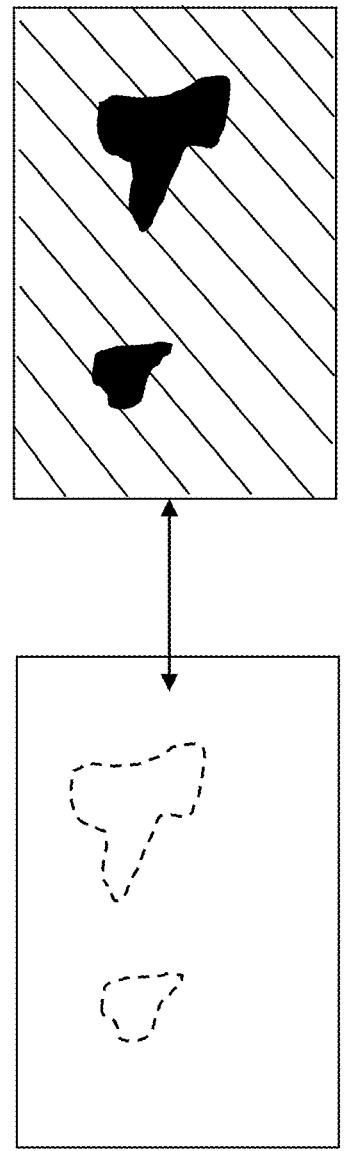

In one embodiment, the one or more graphic indicators may be displayed at intervals, or 'pulsed' to attract the attention of the user Referring to FIGS. 2I-2J, upon scanning over the subject and detecting a feature by feature detector 112, rendering unit 114 may flash a highlight on the detected feature to make it visible, as seen in FIG. 2I. Alternatively, rendering unit 114 may alternately render the blue and white frames at a low frequency over some or all of display 106 as seen in FIG. 2J.

Reference is now made to FIG. 3A which illustrates a schematic diagram of an exemplary method for synchronizing the rendering of the captured frames with the illumination cycle of the lamp, thereby differentiating between white and blue frames. Lamp 104 may be configured to alternately emit white and blue light at a predetermined illuminating frequency, such as by illuminating at cycles comprising of 0.1 s of blue light followed by 0.9 s of white light. The camera of device 100 may capture multiple sequential frames of the subject thus illuminated by lamp 104 and store them in buffer 118. Frame analyzer 110 may differentiate blue frames from white frames by analyzing the frames stored in the buffer in accordance with the illuminating frequency.

In one embodiment, frame analyzer 110 may evaluate a blue level for the incoming frames at a predetermined evaluation frequency. Frame analyzer 110 may categorize a frame as a blue reference frame by determining a peak blue level for the reference frame using any suitable method, such as by determining that the blue level for the frame is the maximum blue level calculated over several illuminating cycles of lamp 104, or by comparing the blue level of the frame to a running average of blue levels and determining the peak blue level, to name a few. Frames whose time stamp indicates they were captured at the same point of the illumination cycle as the blue reference frame, and are thus synchronized with the blue reference frame, may also be categorized as blue. Frames whose time stamp indicates they were captured at a different point of the illumination cycle than the blue reference frame may be categorized as white. The white and blue frames may be rendered separately using any of the techniques described above, thereby synchronizing the rendering of the frames with the illumination cycle of the lamp.

For example, referring to FIG. 3A, the illumination cycle is represented over a time axis 300 with white rectangles 302 representing periods of illumination by white light, and black rectangles 304 representing periods of illumination by blue light. Blue levels 306, illustrated as arrows with differing lengths corresponding to measured blue pixel-per-frame levels, may be evaluated for incoming frames over a time period, such as three seconds corresponding to three cycles of the lamp. The blue levels may be stored in association with the time stamps of the corresponding frames. The maximum blue level 306a may be identified, and the time stamp corresponding to maximum blue level 306a may be used as reference to determine an offset for identifying additional blue frames. Frames 306b and 306c whose time stamp corresponds to an integer cycle of the determined offset may be categorized as blue frames, and the remaining frames may be categorized as white frames.

Figure 3B:
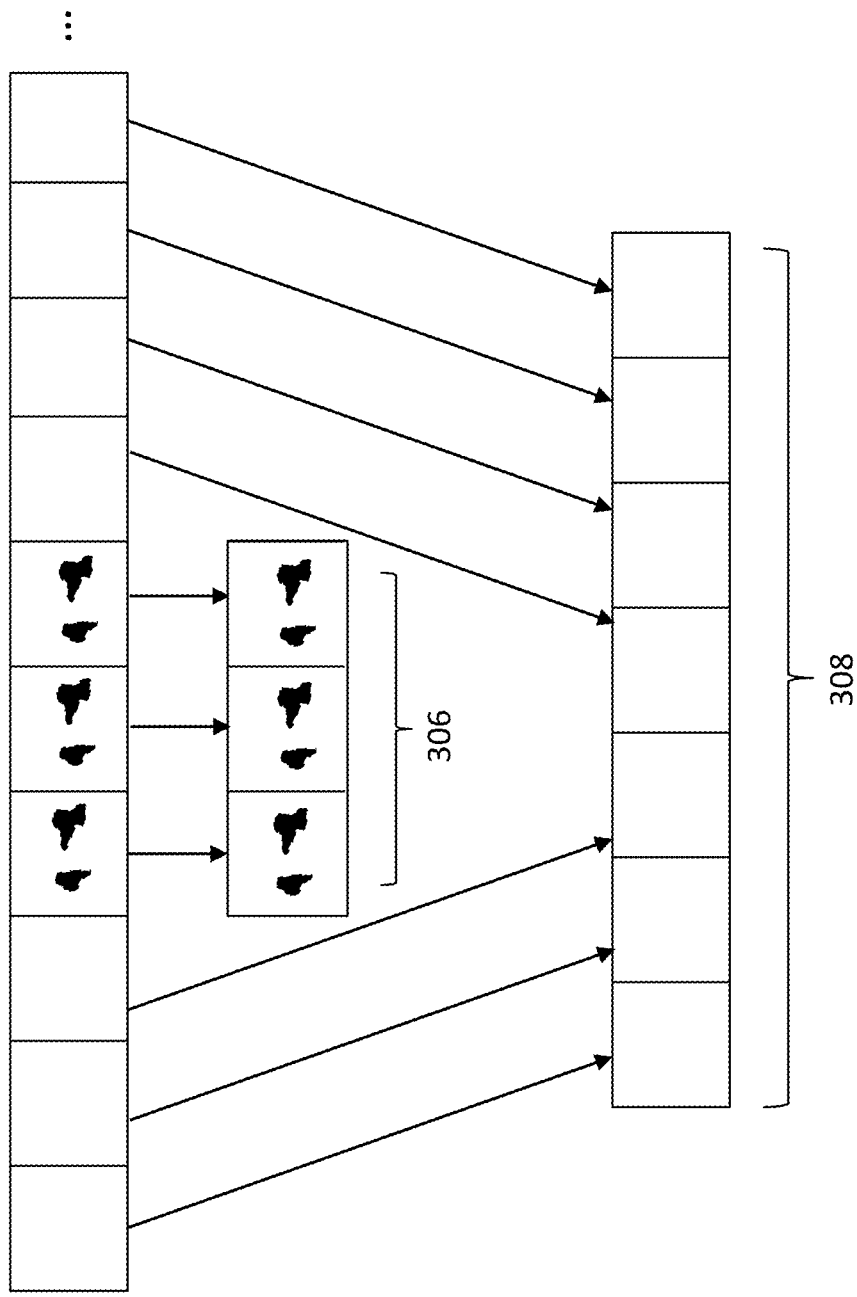

In one embodiment, multiple blue frames 306 may be identified within a single cycle, as shown in FIG. 3B, using any suitable technique, such as by synchronizing the time-stamp of any of frames 306 with the time-stamp of one or more blue reference frames, or by maintaining a running average of blue levels to differentiate multiple blue frames 306 from multiple white frames 308. Thus identified, blue frames 306 and white frames 308 may be stored and/or rendered separately using the methods described above, thereby synchronizing the rendering of the incoming frames with the illuminating frequency.

For example, the system and methods described above may be used to examine a subject to detect one or more indications of assault that may not be visible under regular light, such as bruising beneath the skin or minute traces of semen or blood on the skin's surface, to name a few. A software application for performing the above steps may be loaded onto any suitable mobile device provided with a standard camera. The subject may be illuminated using the lamp disclosed herein, and the device may be used to alternately capture image of the subject under blue illumination and white illumination, differentiate the frames captured under the two illuminations and render the frames separately, to detect a feature that is only visible under blue illumination, and indicate it to the user.

Figure 4:
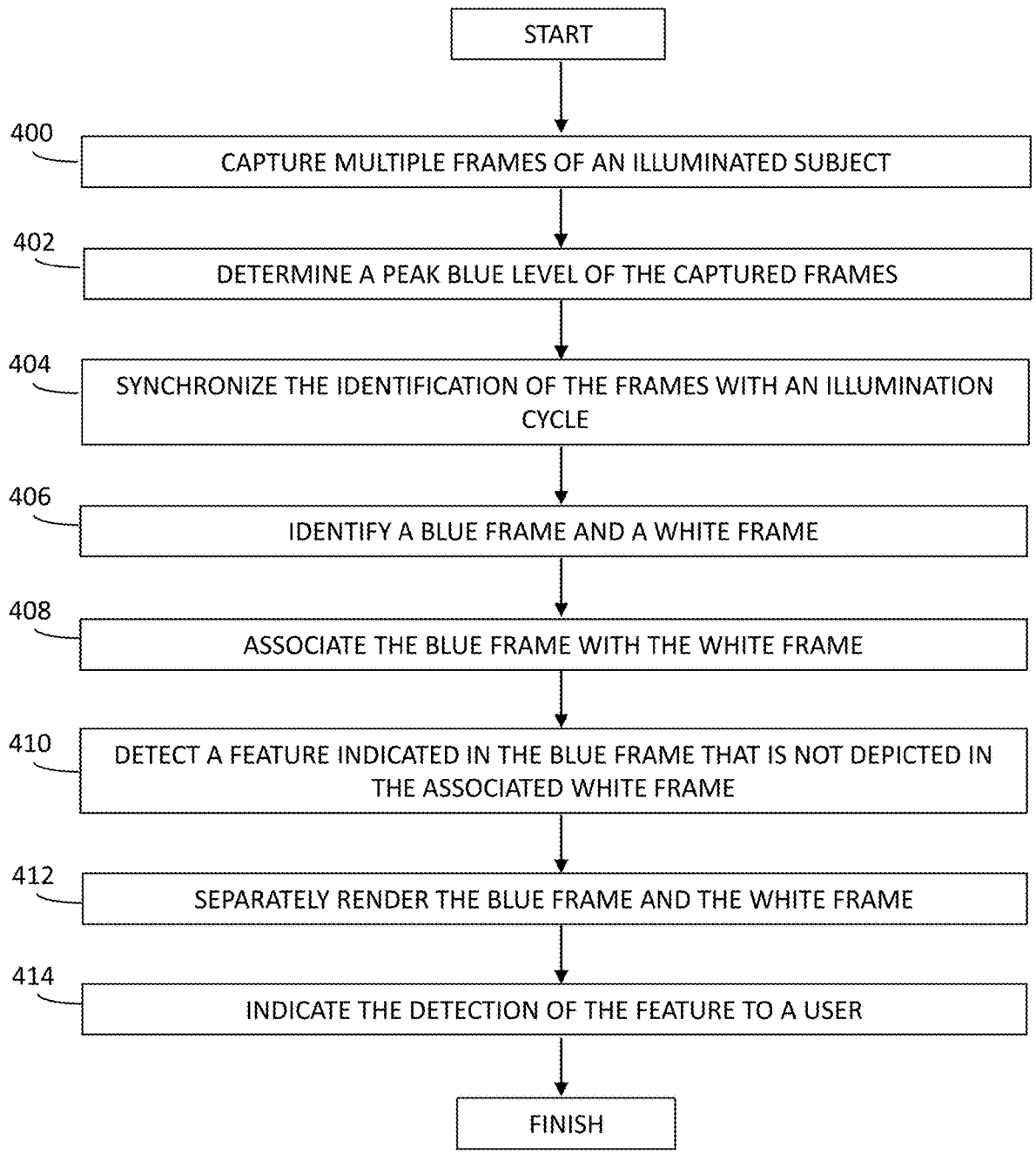
FIG. 4 illustrates a flowchart of a method for the system of FIGS. 1A-D, 2A-J, and 3A-B.

Reference is now made to FIG. 4 which illustrates a flowchart of a method for the system of FIGS. 1A-1D, in accordance with an embodiment. Multiple frames of a subject, illuminated as described above, may be captured by a camera provided with a mobile device and stored in a buffer (Step 400). A peak blue level of the captured frames may be determined and a blue reference frame corresponding to the peak blue level may be identified (Step 402). The identification of the captured frames as blue or white frames may be synchronized with a predefined alternating blue light and white light illumination cycle using a time stamp associated with the captured frames, and a time stamp of the peak blue level corresponding to the blue reference frame (Step 404). A first frame of the multiple captured frames may be identified as a blue frame, where the first frame was captured while the subject was illuminated by blue light, and a second frame of the multiple captured frames may be identified as a white frame, where the second image was captured while the subject was illuminated by white light, such as in accordance with the synchronization step (Step 406). The blue frame may be associated with the white frame, such as by comparing the time-stamps of the respective captured images, or by performing image analysis, or any other suitable method (Step 408). A feature depicted in the blue frame that is not depicted in the associated white frame, such as may be associated with a fluorescing substance, may be detected (Step 410). The blue frame and the white frame may be separately rendered on a user interface display, such as using any of the rendering methods described herein (Step 412). The detection of the feature may be indicated to a user, such as by applying any of the methods described herein (Step 414).

In another embodiment, in addition to blue and white light, the tissue may be intermittently illuminated with multispectral light, to detect and analyze additional absorption and/or scattering properties of the bodily tissue. Wavelengths that indicate the spectral properties of one or more bulk tissue components, such as water ($H_2O$), oxy-hemoglobin ($HbO_2$), deoxy-hemoglobin (Hb), and melanin, may be selected to measure the respective concentrations of these bulk tissue components in the illuminated tissue. The resultant images obtained by the illumination may be overlaid with any of the images obtained using the white and/or blue light using any of the overlaying techniques described above, to indicate the concentrations of any of these components, accordingly.

The wavelengths may be selected using any known technique, such as described in "*Rapid spectral analysis for spectral imaging*", S L Jacques, R Samatham, N Choudhury, *Biomed Opt Expr* 1, 157-164 (2010).

In this exemplary technique, the bodily tissue is illuminated using multiple wavelengths λ and the spectral response of the tissue is measured and fitted to a model that relates the diffuse reflectance, $R_d$, to one or more optical tissue properties, such as the reduced scattering coefficient $\mu_s'$, and/or the absorption coefficient $\mu_a$. Any suitable fitting technique may be used, such as least-squares fitting. These measured optical properties may be mapped to the corresponding optical properties for each of the bulk tissue components to determine which wavelengths λ best indicate their respective concentrations.

Scattering is typically affected by concentrations of tissue components such as collagen fibrils, cell nuclei, and mitochondria, and thus $\mu_s'$ may be used to determine the concentration of these tissue components. Absorption is typically affected by the water and hemoglobin concentrations, and thus, concentration of these components may be determined using $\mu_a$.

The main absorbers of visible and near infrared (NIR) light in tissue are water, $HbO_2$, and Hb, as well as various forms of melanin. The absorbers relating to hemoglobin are of particular interest, since these vary in both location and time. In trying to quantify Hb and $HbO_2$ concentrations, suitable wavelengths fall into 3 categories:

1. Wavelengths that correspond to an absorption peak of either Hb or HbO2
2. Wavelengths in which there are large differences between Hb and HbO2
3. Wavelengths in which the absorption by Hb and HbO2 are equal (isobestic points)

Figure 6A:
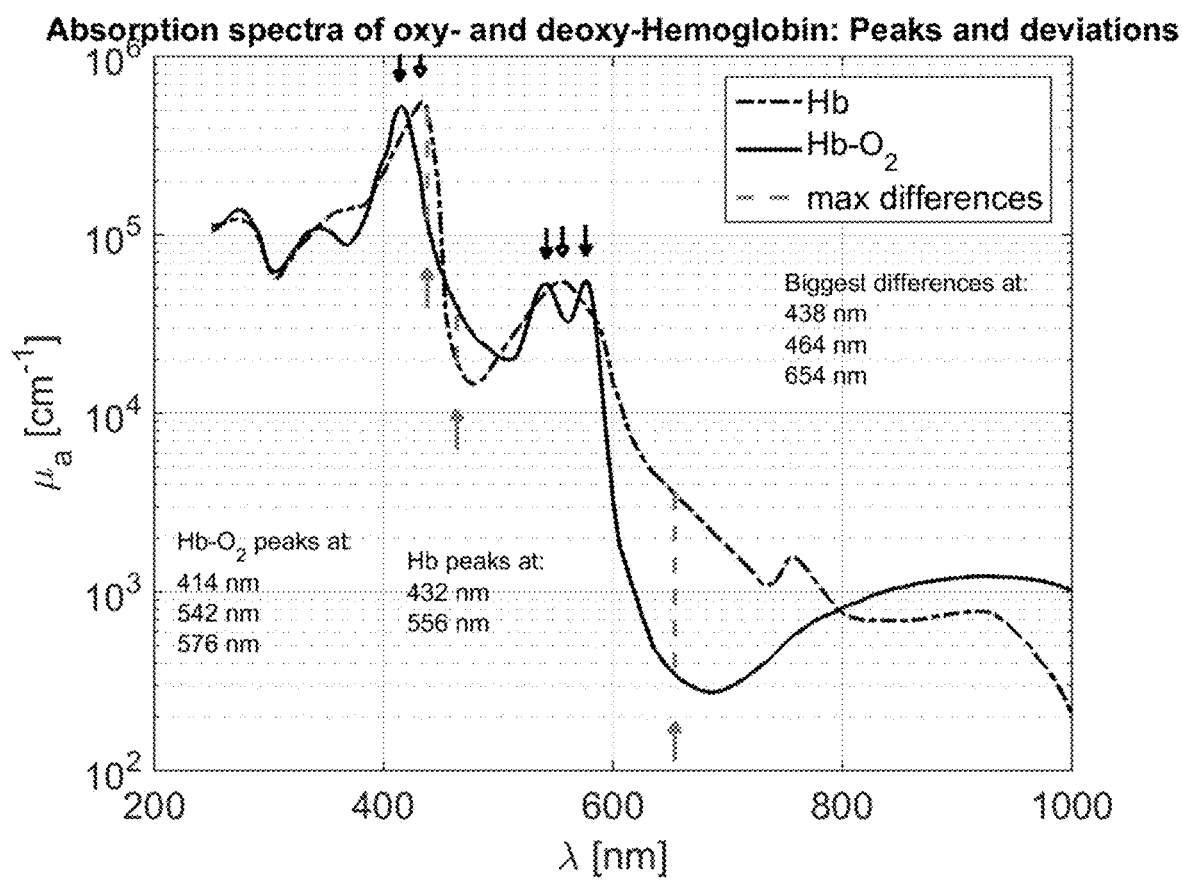
FIGS. 6A-6C show graphs for multi-spectral tissue analysis, in accordance with an embodiment.
Figure 6B:
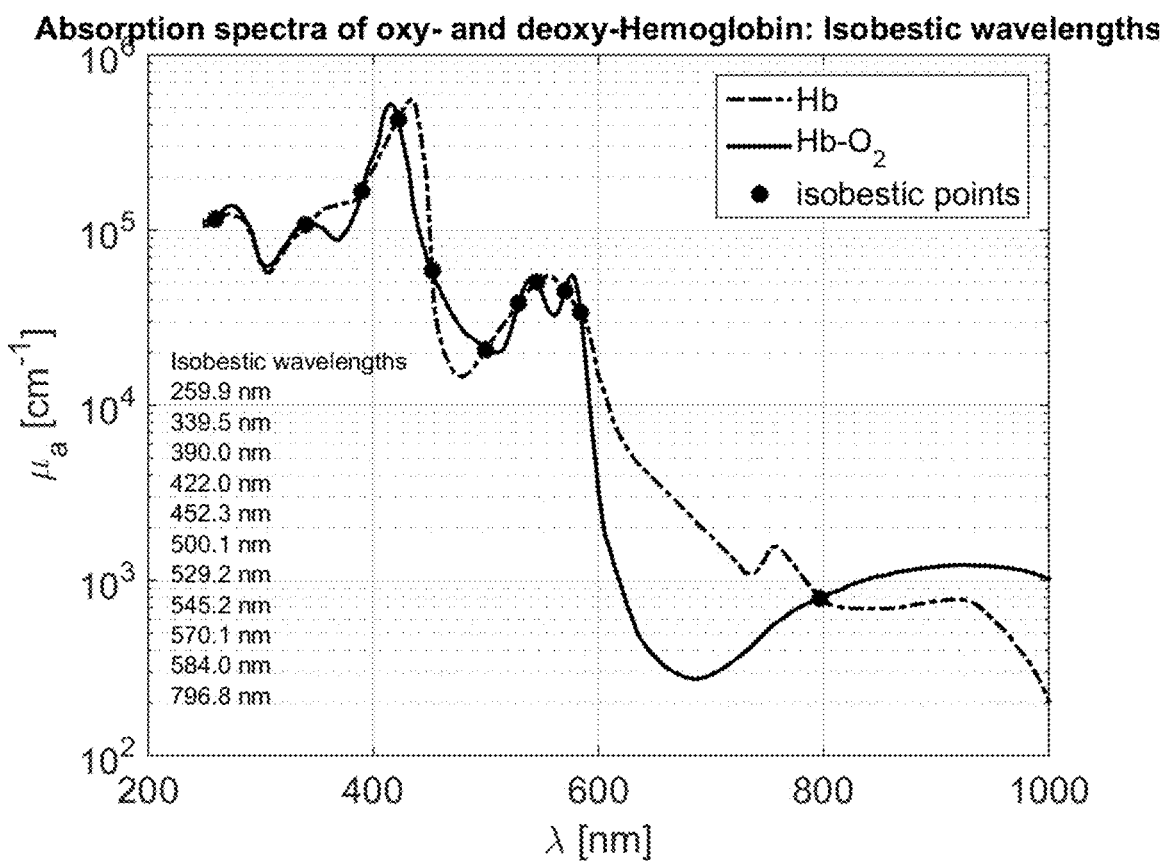

Reference is now made to FIGS. 6A-6B, which show a comparison of absorption spectra for oxy-hemoglobin ($HbO_2$), and deoxy-hemoglobin (Hb). FIG. 6A indicates the peak and deviation points of the absorption spectra for oxy-hemoglobin ($HbO_2$), and deoxy-hemoglobin (Hb), and FIG. 6B indicates their respective isobestic points. As can be seen from FIG. 6A, the wavelengths corresponding to peak absorption spectra for $HbO_2$ are 414 nanometers (nm), 542 nm, and 576 nm; wavelengths corresponding to peak absorption spectra for Hb are 432 nm and 556 nm; and wavelengths corresponding to the peak difference in absorption between $HbO_2$ and Hb are 438 nm, 464 nm, and 654 nm.

Turning to FIG. 6B, the isobestic points for the absorption spectra of $HbO_2$ and Hb, namely, 259.9 nm, 339.5 nm, 390.0 nm, 422.0 nm, 452.3 nm, 500.1 nm, 529.2 nm, 545.2 nm, 570.1 nm, 584.0 nm, 796.8 nm.

Similar graphs may be obtained to determine wavelengths corresponding to peak, maximum deviation, and/or isobestic points for other light absorbing tissue components, such as water, which in the near-infrared range has one such peak absorption at approximately 970 nm. A similar analysis may be conducted to determine the ideal wavelengths for indicating concentrations of melanin.

To analyze scattering, it is noted that for a given defined wavelength range of visible light, and a consistent size for cellular structures, such as nuclei and mitochondria, and collagen cross-links in the extracellular matrix, the reduced scattering coefficient $\mu_s'$ decreases with respect to wavelength λ. The following formula may be used to quantify the decrease in scattering:

$$\mu_s'(\lambda) = \mu_s'(\lambda_0)\left[f\left(\frac{\lambda}{\lambda_0}\right)^{-4} + (1-f)\left(\frac{\lambda}{\lambda_0}\right)^{-b}\right] \quad (1)$$

Where $\lambda_0$ is a reference wavelength used for calibration purposes, the term $$f\left(\frac{\lambda}{\lambda_0}\right)^{-4}$$

refers to the contribution from Rayleigh scattering resulting from smaller particles, such as collagen fibrils, cytoskeletal proteins and the like, and the term $$(1-f)\left(\frac{\lambda}{\lambda_0}\right)^{-b}$$

refers to the contribution from Mie scattering resulting from larger particles, such as nuclei and mitochondria, and b is a decay constant.

The reference wavelength $\lambda_0$ may depend on the sensitivity of the detection system, and may be selected to yield a Rayleigh scattering contribution that is at least 10% of the Mie scattering contribution. Typically, both the detection and computational criteria are met when illuminating at wavelengths ranging between 450-550 nm.

Thus, to utilize the scattering spectra for multi-spectral tissue imaging, three or more wavelengths may be selected from the following ranges:
  Around the reference wavelength ($\lambda=\lambda_0$), corresponding to 450-550 nm,
  At a wavelength lower than the reference wavelength $\lambda<\lambda_0$), corresponding to 400-450 nm, and
  At a wavelengths higher than the reference wavelength $\lambda>\lambda_0$), corresponding to 550-750 nm. Multiple wavelengths may be used in this range to account for the decay constant b.

Figure 6C:
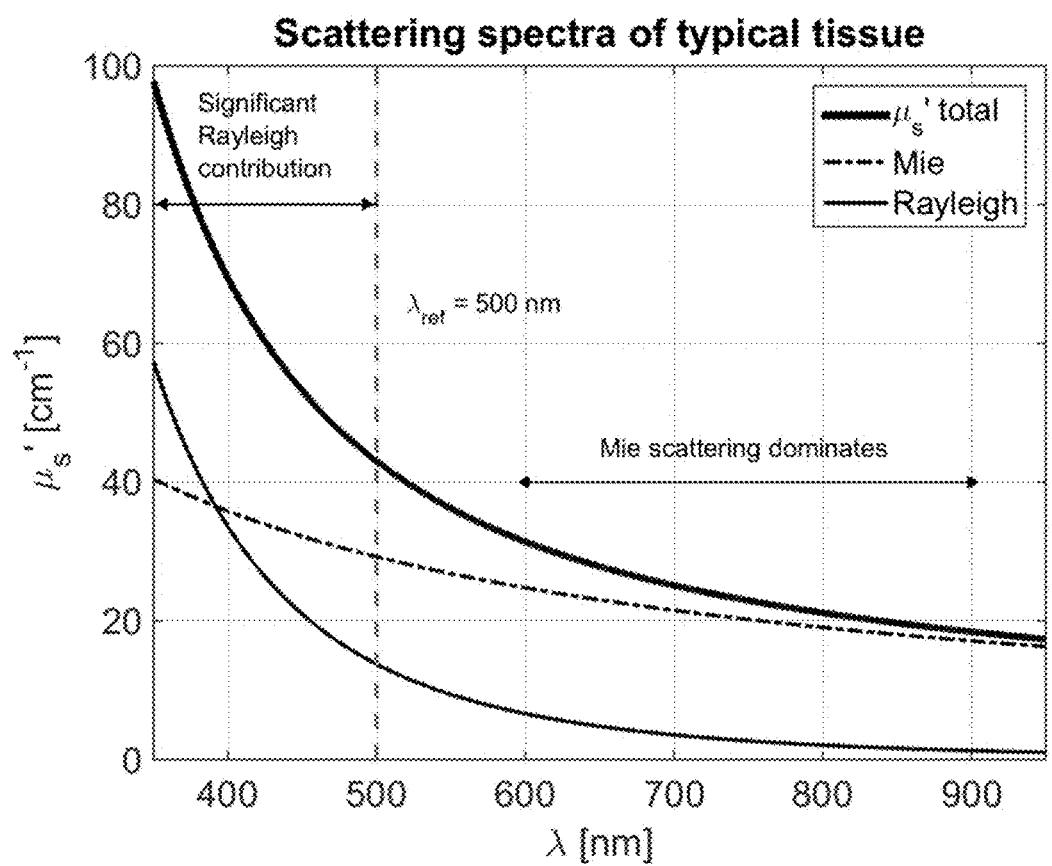

Referring to FIG. 6C, total, Rayleigh, and Mie scattering coefficients for a typical bodily tissue is shown for a range of wavelengths. As can be seen from FIG. 6C, at wavelengths below 500 nm, a significant portion of the total scattering may be attributable to Rayleigh scattering, and at wavelengths above 500 nm, the Mie scattering component is the dominant portion of the total scattering. Thus, 500 nm may be a useful threshold for selecting different wavelengths with which to illuminate the tissue for determining concentrations of scattering-sensitive tissue components.

It may be noted that any of the aforementioned wavelength values may refer to approximations.

Lamp 104 may be provided with additional light sources (not shown), each configured to illuminate subject 102 with any of the above listed wavelengths intermittently with white light. Thus, if n-wavelengths are selected to illuminate subject 102, a total illumination cycle may have a duration of n seconds: 0.1 s for each wavelength $\lambda$ followed by 0.9 s of white light, allowing the user to view the illuminated subject 102 under white light, while detecting any components sensitive to the multi-spectral light. The illumination cycle may be synchronized with respect to each of the selected multi-spectral wavelengths using the method described above with reference to FIGS. 3A-3B, by detecting peak multi-spectral illumination levels for any of the captured frames, and synchronizing their respective timestamps with a predefined illumination cycle. The images obtained using the multi-spectral illumination may be analyzed via frame analyzer 110 and compared against the frames obtained using the white light and/or blue light, to detect one or more features of interest that are not depicted in any of the white and/or blue frames. Detected features, such as associate with any of: a fluorescing substance, water, Hb, $HbO_2$, collagen fibrils, cytoskeletal proteins, nuclei and mitochondria, may be indicated to the user on display 106 of device 100 using any of the techniques described above, such as described in FIGS. 2A-2J, and/or with an audio-indicator Optionally, the multi-spectral wavelength value (in nm) used to illuminate the subject, and/or the wavelength-sensitive component, such as 'water', 'Hb', or '$HbO_2$', or other any of the above-mentioned components, may be indicated with the indicated feature, such as at a corner of display 106.

Additionally, or alternatively, one or more polarized images of the subject may be used to detect the biological substance. For example, polarization difference imaging (PDI), may be applied to acquire discern the biological substance and/or an attribute thereof. PDI systems allow capturing images of a subject under different polarizations, such as by acquiring an image $I_{PAR}$ under parallel polarized illumination, and an image $I_{PER}$ under orthogonal, or perpendicular polarized illumination. The difference between $I_{PAR}$ and $I_{PER}$, comprising the PDI image, may reveal structures in the superficial single scattering layer, by eliminating the broad halo caused by diffuse light that penetrated the deeper tissue layers. Because it reveals structures that cannot be seen under normal white light illumination, the PDI image may be comparable to the fluorescent image described above. Thus, structures hidden under white light illumination may be identified in the PDI image and displayed using any of the display methods described above with respect to FIGS. 2A-2J.

Figure 7A:
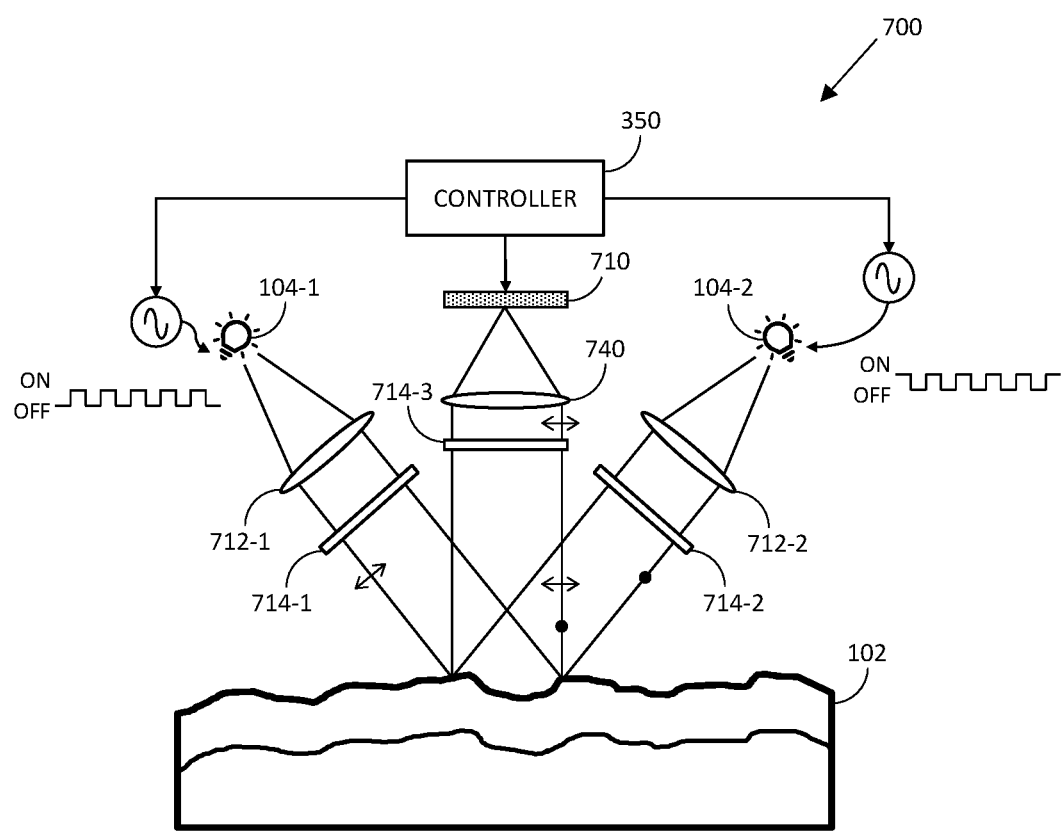
FIGS. 7A-7B each show an apparatus for acquiring one or more polarization difference imaging (PDI) images and which may be integrated with the system of FIG. 1A, in accordance with an embodiment.
Figure 7B:
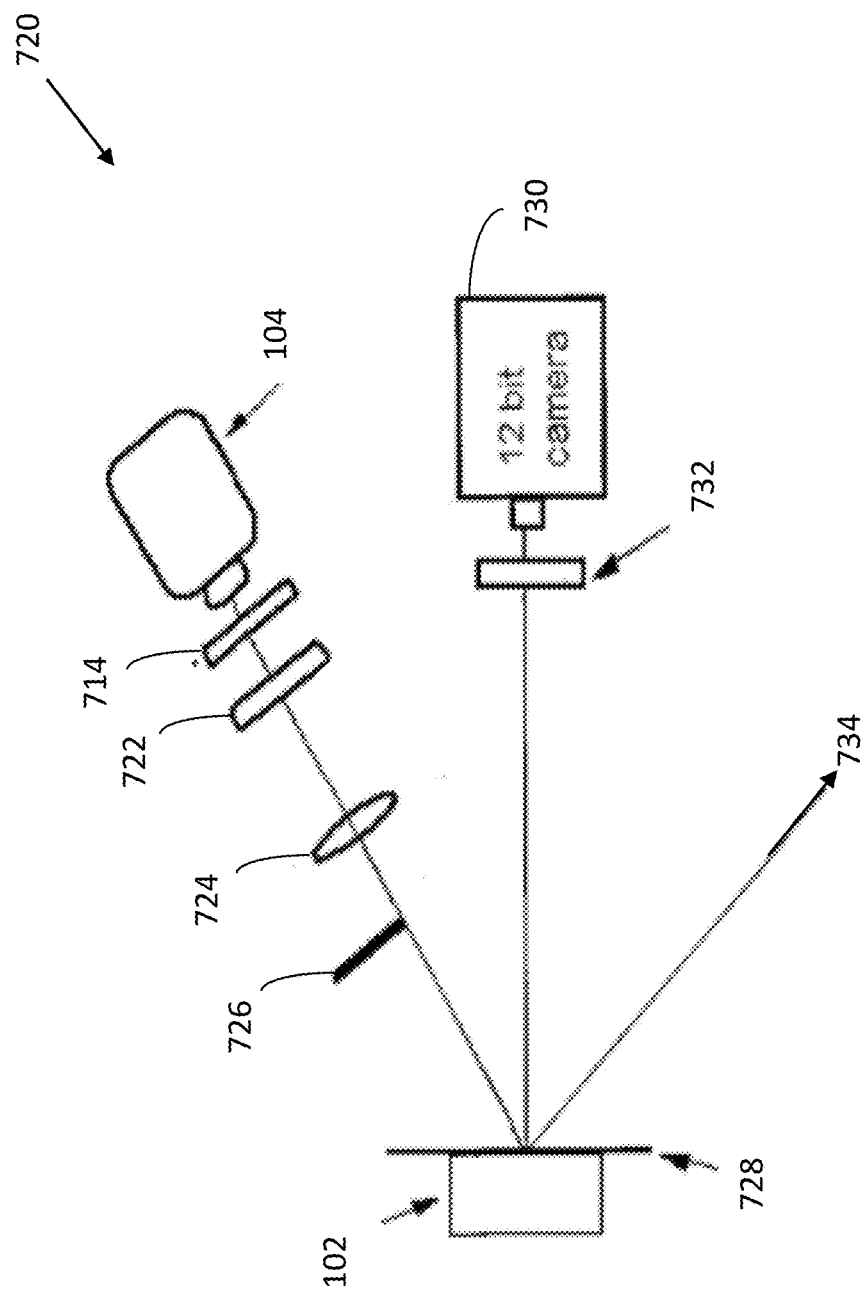

Reference is now made to FIGS. 7A-7B which each show an exemplary apparatus for acquiring one or more polarization difference imaging (PDI) images and which may be integrated with the system of FIG. 1A, in accordance with an embodiment. It may be appreciated that the systems of FIGS. 7A-7B are but two implementations for acquiring a PDI image, and that other suitable systems may be used, accordingly.

Referring to FIG. 7A an optical apparatus 700 is shown similar to that described in "Polarized light imaging apparatus and methods thereof for separating light from a surface of a sample its deeper diffuse layers", US Patent US20160084751, Levitz et al, for acquiring one or more PDI images. Any of the components of system 700 may be integrated with device 100, or may be provided separately.

System 700 may include multiple light sources 104-1 and 104-2 coupled with illuminating optic lenses 712-1 and 712-2 and polarizers 714-1 and 714-2, respectively, for illuminating subject 102 using polarized light via multiple, separate optical paths. Each of light sources 104-1 and 104-2 may be controlled by a processor, or controller 350 to produce differently polarized light beams for illuminating subject 102. Light sources 104-1 and 104-2 may produce an oscillating signal, such as an oscillating 'on-off' step function. A polarizer 714-3 and detection optic lens 740 may be provided in the optical path between subject 102 and a polarization sensitive optical detector 710.

Polarizers 714-1 and 714-3 may be parallel to each other, and polarizers 714-2 and 714-3 may be orthogonal to each other, allowing each of a parallel polarized image $I_{PAR}$ and a perpendicular polarized image $I_{PER}$ of subject 102 to be captured by detector 710, either simultaneously or sequentially via each of the optical paths, as described in Levitz et al. (US Patent US20160084751). For example, each frame for each polarization type may be captured either by coordinating the illumination by light sources 104-1 and 104-2 according to a predetermined time interval, or by distinguishing between polarization states based on predetermined markers interspersed between the unique polarization states.

Reference is now made to FIG. 7B, which shows an optical apparatus 720, similar to that described in S L Jacques, J C Ramella-Roman, K Lee, "*Imaging skin pathology with polarized light*", *Journal of Biomedical Optics* 7(3), 329-340 (July 2002), for acquiring one or more PDI images, and which may be integrated with the system of FIG. 1A, in accordance with an embodiment. Any of the components of system 720 may be integrated with device 100, or may be provided separately.

System 720 includes light source 104, such as a white light source, optically coupled with a source polarizer 714, color filter 722, and collimating lens 724 disposed along the optical path between light source 104 and subject 102. Source polarizer 714 may be oriented parallel to the plane of light source 104 and/or subject 102. Optionally, a razor blade 726 may be positioned between collimating lens 724 and subject 102. A glass plate 728 coupled to subject 102, such as with a drop of water, may be positioned between subject 102 and both of light source 104 and a camera 730, such that specular reflectance 734 from any of air, glass plate 728, or subject 102 may be reflected away from camera 730. An analyzing polarizer 732 may be positioned along the optical path between subject 102 and camera 730. Analyzing polarizer 732 may be alternately oriented parallel or perpendicular to the orientation of the source polarizer 714, such as by positioning multiple polarizers 732 at different orientations along the optical path between subject 102 and camera 730, or by reorienting any of polarizers 714 and 732 using mechanical means, or other suitable techniques, to allow camera 730 to capture two images of subject 102: a parallel polarized image, $I_{PAR}$, and a perpendicular polarized image $I_{PER}$.

Polarized, filtered and collimated light originating from source 104 may enter subject 102 and backscatter through polarizer 732 to camera 730, yielding the two images $I_{PAR}$ and $I_{PER}$.

The captured frames, $I_{PAR}$ and $I_{PER}$ may be analyzed by processor 350, such as may comprise the processor of device 100, and the PDI image, comprising the difference between $I_{PAR}$ and $I_{PER}$, may be determined. The processor may detect a structure, or PDI feature of subject 102 that is depicted in the PDI image, but was not detected in any of the blue and white frames of subject 102 acquired above. The detection of the PDI feature may be indicated to the user by applying any of the techniques described above, such as by implementing any of a visual, audio, or vibration indication. Additionally, or alternatively, the PDI feature may be displayed on the user interface by highlighting and/or overlaying the PDI feature on the white light image, similar to the techniques described above with respect to FIGS. 2A-2J.

It may be appreciated that additional imaging modalities, such as Degree of Polarization imaging, or some variation of Mueller Matrix imaging, may be used accordingly as a substitute to the PDI images.

Figure 5:
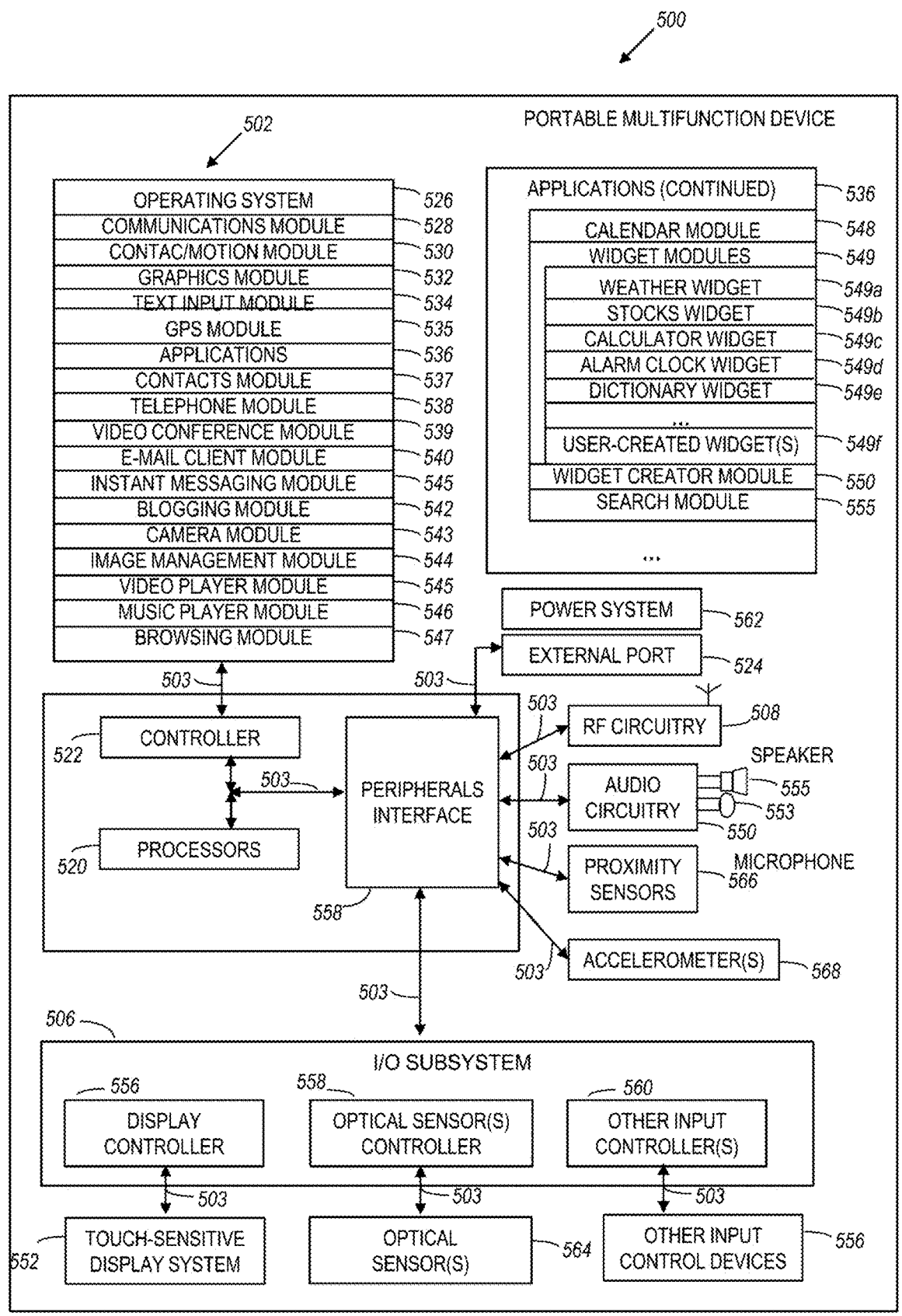
FIG. 5 shows a block diagram of a portable multifunction device, in accordance with an embodiment.

Reference is now made to FIG. 5, which shows a block diagram of a portable multifunction device (also "handheld electronic device" or simply "device") 500, corresponding to device 100 of FIGS. 1A-1D, in accordance with some embodiments.

Device 500 may store in a non-volatile memory thereof a software application configured to operate in the framework the system described herein. The software application may include instructions for receiving and analyzing multiple frames captured by a camera. This receiving and analyzing multiple captured frames may include operating a processing unit (also "hardware processor", "CPU" or simply "processor") of device 500 to receive the multiple images from a camera of the device.

Device 500 may be equipped with a touch-sensitive display 552. The touch-sensitive display 552 is sometimes called a "touch screen" for convenience, and may also be known as or called a touch-sensitive display system. Touch-sensitive display 552 may be configured to detect to an indication by a user to switch to a different rendering setting, as described above. Device 500 may include a memory 502 (which may include one or more computer readable storage mediums), such as may correspond to storage device 116 described above, and/or a memory controller 522, one or more processing units (CPUs) 520, a peripherals interface 558, RF circuitry 508, audio circuitry 550, a speaker 555, a microphone 553, an input/output (I/O) subsystem 506, other input or control devices 556, and an external port 524. Device 500 may include one or more optical sensors 564. These components may communicate over one or more communication buses or signal lines 503.

It should be appreciated that device 500 is only one example of a portable multifunction device 500, and that device 500 may have more or fewer components than shown, may combine two or more components, or a may have a different configuration or arrangement of the components. The various components shown in FIG. 4 may be implemented in hardware, software or a combination of both hardware and software, including one or more signal processing and/or application specific integrated circuits.

Memory 502 may include high-speed random access memory and may also include non-volatile memory, such as one or more magnetic disk storage devices, flash memory devices, or other non-volatile solid-state memory devices. Access to memory 502 by other components of device 500, such as the CPU 520 and the peripherals interface 558, may be controlled by the memory controller 522.

The peripherals interface 558 couples the input and output peripherals of the device to the CPU 520 and memory 502. The one or more processors 520 run or execute various software programs and/or sets of instructions stored in memory 502 to perform various functions for device 500 and to process data.

In some embodiments, the peripherals interface 558, the CPU 520, and the memory controller 522 may be implemented on a single chip, such as a chip 504. In some other embodiments, they may be implemented on separate chips.

The RF (radio frequency) circuitry 508 receives and sends RF signals, also called electromagnetic signals. The RF circuitry 508 converts electrical signals to/from electromagnetic signals and communicates with communications networks and other communications devices via the electromagnetic signals. The RF circuitry 508 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 508 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.55a, IEEE 802.55b, IEEE 802.55g, and/or IEEE 802.55n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 550, the speaker 555, and the microphone 553 provide an audio interface between a user and device 500. The audio circuitry 550 receives audio data from the peripherals interface 558, converts the audio data to an electrical signal, and transmits the electrical signal to the speaker 555. The speaker 555 converts the electrical signal to human-audible sound waves. The audio circuitry 550 also receives electrical signals converted by the microphone 553 from sound waves. The audio circuitry 550 converts the electrical signal to audio data and transmits the audio data to the peripherals interface 558 for processing. Audio data may be retrieved from and/or transmitted to memory 502 and/or the RF circuitry 508 by the peripherals interface 558. In some embodiments, the audio circuitry 550 also includes a headset jack. The headset jack provides an interface between the audio circuitry 550 and removable audio input/output peripherals, such as output-only headphones or a headset with both output (e.g., a headphone for one or both ears) and input (e.g., a microphone).

The I/O subsystem 506 couples input/output peripherals on device 500, such as the touch screen 552 and other input/control devices 556, to the peripherals interface 558. The I/O subsystem 506 may include a display controller 556 and one or more input controllers 560 for other input or control devices. The one or more input controllers 560 receive/send electrical signals from/to other input or control devices 556. The other input/control devices 556 may include physical buttons (e.g., push buttons, rocker buttons, etc.), dials, slider switches, joysticks, click wheels, and so forth. In some alternate embodiments, input controller(s) 560 may be coupled to any (or none) of the following: a keyboard, infrared port, USB port, and a pointer device such as a mouse. The one or more buttons may include an up/down button for volume control of the speaker 555 and/or the microphone 553. The one or more buttons may include a push button A quick press of the push button may disengage a lock of the touch screen 552 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button may turn power to device 500 on or off. The user may be able to customize a functionality of one or more of the buttons. The touch screen 552 is used to implement virtual or soft buttons and one or more soft keyboards.

The touch-sensitive touch screen 552 provides an input interface and an output interface, corresponding to display 106 comprising primary portion 106a and secondary portion 106b described above, between the device and a user. The display controller 556 receives and/or sends electrical signals from/to the touch screen 552. The touch screen 552 displays visual output to the user. The visual output may include graphics, text, icons, video, and any combination thereof (collectively termed "graphics"). In some embodiments, some or all of the visual output may correspond to user-interface objects, further details of which are described below. The display controller 556 may be configured to divide touch screen 552 into multiple portions for separate and simultaneous rendering blue and white frames, as described herein.

A touch screen 552 has a touch-sensitive surface, sensor or set of sensors that accepts input from the user based on haptic and/or tactile contact. The touch screen 552 and the display controller 556 (along with any associated modules and/or sets of instructions in memory 502) detect contact (and any movement or breaking of the contact) on the touch screen 552 and converts the detected contact into interaction with user-interface objects (e.g., one or more soft keys, icons, web pages or images) that are displayed on the touch screen. In an exemplary embodiment, a point of contact between a touch screen 552 and the user corresponds to a finger of the user.

The touch screen 552 may use LCD (liquid crystal display) technology, or LPD (light emitting polymer display) technology, although other display technologies may be used in other embodiments. The touch screen 552 and the display controller 556 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 552.

A touch-sensitive display in some embodiments of the touch screen 552 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0055024A5, each of which is hereby incorporated by reference in their entirety. However, a touch screen 552 displays visual output from the portable device 500, whereas touch sensitive tablets do not provide visual output.

A touch-sensitive display in some embodiments of the touch screen 552 may be as described in the following applications: (5) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 552 may have a resolution in excess of 500 dpi. In an exemplary embodiment, the touch screen has a resolution of approximately 560 dpi. The user may make contact with the touch screen 552 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 500 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 552 or an extension of the touch-sensitive surface formed by the touch screen.

In some embodiments, device 500 may include a physical or virtual click wheel as an input control device 556. A user may navigate among and interact with one or more graphical objects (henceforth referred to as icons) displayed in the touch screen 552 by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the user may press down on at least a portion of the click wheel or an associated button. User commands and navigation commands provided by the user via the click wheel may be processed by an input controller 560 as well as one or more of the modules and/or sets of instructions in memory 502. For a virtual click wheel, the click wheel and click wheel controller may be part of the touch screen 552 and the display controller 556, respectively. For a virtual click wheel, the click wheel may be either an opaque or semi-transparent object that appears and disappears on the touch screen display in response to user interaction with the device. In some embodiments, a virtual click wheel is displayed on the touch screen of a portable multifunction device and operated by user contact with the touch screen.

Device 500 also includes a power system 562 for powering the various components. The power system 562 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 500 may also include one or more optical sensors 564. FIG. 9 shows an optical sensor coupled to an optical sensor controller 558 in I/O subsystem 506. The optical sensor 564 may include charge-coupled device (CCD) or complementary metal-oxide semiconductor (CMOS) phototransistors. The optical sensor 564 receives light from the environment, projected through one or more lens, and converts the light to data representing an image. In conjunction with an imaging module 543 (also called a camera module), the optical sensor 564 may capture still images or video, corresponding to the captured frames described herein. In some embodiments, an optical sensor is located on the back of device 500, opposite the touch screen display 552 on the front of the device, so that the touch screen display may be used as a viewfinder for either still and/or video image acquisition. In some embodiments, an optical sensor is located on the front of the device so that the user's image may be obtained for videoconferencing while the user views the other video conference participants on the touch screen display. In some embodiments, the position of the optical sensor 564 can be changed by the user (e.g., by rotating the lens and the sensor in the device housing) so that a single optical sensor 564 may be used along with the touch screen display for both video conferencing and still and/or video image acquisition.

Device 500 may also include one or more proximity sensors 566. FIG. 4 shows a proximity sensor 566 coupled to the peripherals interface 558. Alternately, the proximity sensor 566 may be coupled to an input controller 560 in the I/O subsystem 506. The proximity sensor 566 may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 11/620,702, "Using Ambient Light Sensor To Augment Proximity Sensor Output", filed Jan. 7, 2017; Ser. No. 11/586,862, "Automated Response To And Sensing Of User Activity In Portable Devices," filed Oct. 24, 2006; and Ser. No. 11/638,251, "Methods And Systems For Automatic Configuration Of Peripherals," filed Dec. 12, 2006, which are hereby incorporated by reference in their entirety. In some embodiments, the proximity sensor turns off and disables the touch screen 552 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

Device 500 may also include one or more accelerometers 568. FIG. 4 shows an accelerometer 568 coupled to the peripherals interface 558. Alternatively, the accelerometer 568 may be coupled to an input controller 560 in the I/O subsystem 506. The accelerometer 568 may perform as described in U.S. Patent Publication No 2005/0190059, "Acceleration-based Theft Detection System for Portable Electronic Devices," filed on Mar. 1, 2004, and U.S. Patent Publication No. 2006/0017692, "Methods And Apparatuses For Operating A Portable Device Based On An Accelerometer," filed on Nov. 12, 2004 both of which are which are incorporated by reference in their entirety. In some embodiments, information is displayed on the touch screen display in a portrait view or a landscape view based on an analysis of data received from the one or more accelerometers.

In some embodiments, the software components stored in memory 502 may include an operating system 526, a communication module (or set of instructions) 528, a contact/motion module (or set of instructions) 530, a graphics module (or set of instructions) 532, a text input module (or set of instructions) 534, a Global Positioning System (GPS) module (or set of instructions) 535, and applications (or set of instructions) 536.

The operating system 526 (e.g., Android, RTXC, Linux, Unix, OS X, Windows, or an embedded operating system such as VxWorks) includes various software components and/or drivers for controlling and managing general system tasks (e.g., memory management, storage device control, power management, etc.) and facilitates communication between various hardware and software components.

The communication module 528 facilitates communication with other devices over one or more external ports 524 and also includes various software components for handling data received by the RF circuitry 508 and/or the external port 524. The external port 524 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 530 may detect contact with the touch screen 552 (in conjunction with the display controller 556) and other touch sensitive devices (e.g., a touchpad or physical click wheel). The contact/motion module 530 includes various software components for performing various operations related to detection of contact, such as determining if contact has occurred, determining if there is movement of the contact and tracking the movement across the touch screen 552, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 530 and the display controller 556 also detects contact on a touchpad. In some embodiments, the contact/motion module 530 and the controller 560 detects contact on a click wheel.

The graphics module 532 includes various known software components for rendering and displaying graphics on the touch screen 552, including components for changing the intensity of graphics that are displayed, and including the graphic indicators and frame rendering options described herein. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement, and informs the user of an action that has been performed (such as moving an email message to a folder). In this context, a respective animation that confirms an action by the user of the device typically takes a predefined, finite amount of time, such as an amount of time between 0.2 and 5.0 seconds, or between 0.5 and 2.0 seconds, depending on the context.

The text input module 534, which may be a component of graphics module 532, provides soft keyboards for entering text in various applications (e.g., contacts 537, e-mail 540, IM 545, blogging 542, browser 547, and any other application that needs text input).

The GPS module 535 determines the location of the device and provides this information for use in various applications (e.g., to telephone 538 for use in location-based dialing, to camera 543 and/or blogger 542 as picture/video metadata, and to applications that provide location-based services such as weather widgets, local yellow page widgets, and map/navigation widgets).

The applications 536 may include the following modules (or sets of instructions), or a subset or superset thereof:
 a contacts module 537 (sometimes called an address book or contact list);
 a telephone module 538;
 a video conferencing module 539;
 an e-mail client module 540;
 an instant messaging (IM) module 545;
 a blogging module 542;
 a camera module 543 for still and/or video images;
 an image management module 544;
 a video player module 545;
 a music player module 546;
 a browser module 547;
 a calendar module 548;
 widget modules 549, which may include weather widget 549*a*, stocks widget 549*b*, calculator widget 549*c*, alarm clock widget 549*d*, dictionary widget 549*e*, and other widgets obtained by the user, as well as user-created widgets 549*f*;
 widget creator module 550 for making user-created widgets 549*f*;
 search module 555;
 video and music player module 552, which merges video player module 545 and music player module 546;
 notes module 553; and/or
 map module 554.

Examples of other applications 536 that may be stored in memory 502 include other word processing applications, JAVA-enabled applications, encryption, digital rights management, voice recognition, and voice replication.

In conjunction with touch screen 552, display controller 556, contact module 530, graphics module 532, and text input module 534, the contacts module 537 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 538, video conference 539, e-mail 540, or IM 545; and so forth. Embodiments of user interfaces and associated processes using contacts module 537 are described further below.

In conjunction with RF circuitry 508, audio circuitry 550, speaker 555, microphone 553, touch screen 552, display controller 556, contact module 530, graphics module 532, and text input module 534, the telephone module 538 may be used to enter a sequence of characters corresponding to a telephone number, access one or more telephone numbers in the address book 537, modify a telephone number that has been entered, dial a respective telephone number, conduct a conversation and disconnect or hang up when the conversation is completed. As noted above, the wireless communication may use any of a plurality of communications standards, protocols and technologies. Embodiments of user interfaces and associated processes using telephone module 538 are described further below.

In conjunction with RF circuitry 508, audio circuitry 550, speaker 555, microphone 553, touch screen 552, display controller 556, optical sensor 564, optical sensor controller 558, contact module 530, graphics module 532, text input module 534, contact list 537, and telephone module 538, the videoconferencing module 539 may be used to initiate, conduct, and terminate a video conference between a user and one or more other participants.

In conjunction with RF circuitry 508, touch screen 552, display controller 556, contact module 530, graphics module 532, and text input module 534, the e-mail client module 540 may be used to create, send, receive, and manage e-mail. In conjunction with image management module 544, the e-mail module 540 makes it very easy to create and send e-mails with still or video images taken with camera module 543. Embodiments of user interfaces and associated processes using e-mail module 540 are described further below.

In conjunction with RF circuitry 508, touch screen 552, display controller 556, contact module 530, graphics module 532, and text input module 534, the instant messaging module 545 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS). Embodiments of user interfaces and associated processes using instant messaging module 545 are described further below.

In conjunction with RF circuitry 508, touch screen 552, display controller 556, contact module 530, graphics module 532, text input module 534, image management module 544, and browsing module 547, the blogging module 542 may be used to send text, still images, video, and/or other graphics to a blog (e.g., the user's blog).

In conjunction with touch screen 552, display controller 556, optical sensor(s) 564, optical sensor controller 558, contact module 530, graphics module 532, and image management module 544, the camera module 543 may be used to capture still images or video (including a video stream) and store them into memory 502, corresponding to buffer 116 of FIG. 1D, modify characteristics of a still image or video, or delete a still image or video from memory 502. Embodiments of user interfaces and associated processes using camera module 543 are described further below.

In conjunction with touch screen 552, display controller 556, contact module 530, graphics module 532, text input module 534, and camera module 543, the image management module 544 may be used to arrange, modify or otherwise manipulate, label, delete, present (e.g., in a digital slide show or album), and store still and/or video images. Embodiments of user interfaces and associated processes using image management module 544 are described further below.

In conjunction with touch screen 552, display controller 556, contact module 530, graphics module 532, audio circuitry 550, and speaker 555, the video player module 545 may be used to display, present or otherwise play back videos (e.g., on the touch screen or on an external, connected display via external port 524). Embodiments of user interfaces and associated processes using video player module 545 are described further below.

In conjunction with touch screen 552, display system controller 556, contact module 530, graphics module 532, audio circuitry 550, speaker 555, RF circuitry 508, and browser module 547, the music player module 546 allows the user to download and play back recorded music and other sound files stored in one or more file formats, such as MP3 or AAC files. In some embodiments, device 500 may include the functionality of an MP3 player, such as an iPod (trademark of Apple Computer, Inc.). Embodiments of user interfaces and associated processes using music player module 546 are described further below.

In conjunction with RF circuitry 508, touch screen 552, display system controller 556, contact module 530, graphics module 532, and text input module 534, the browser module 547 may be used to browse the Internet, including searching, linking to, receiving, and displaying web pages or portions thereof, as well as attachments and other files linked to web pages. Embodiments of user interfaces and associated processes using browser module 547 are described further below.

In conjunction with RF circuitry 508, touch screen 552, display system controller 556, contact module 530, graphics module 532, text input module 534, e-mail module 540, and browser module 547, the calendar module 548 may be used to create, display, modify, and store calendars and data associated with calendars (e.g., calendar entries, to do lists, etc.). Embodiments of user interfaces and associated processes using calendar module 548 are described further below.

In conjunction with RF circuitry 508, touch screen 552, display system controller 556, contact module 530, graphics module 532, text input module 534, and browser module 547, the widget modules 549 are mini-applications that may be downloaded and used by a user (e.g., weather widget 549a, stocks widget 549b, calculator widget 549c, alarm clock widget 549d, and dictionary widget 549e) or created by the user (e.g., user-created widget 549f). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 508, touch screen 552, display system controller 556, contact module 530, graphics module 532, text input module 534, and browser module 547, the widget creator module 550 may be used by a user to create widgets (e.g., turning a user-specified portion of a web page into a widget).

In conjunction with touch screen 552, display system controller 556, contact module 530, graphics module 532, and text input module 534, the search module 555 may be used to search for text, music, sound, image, video, and/or other files in memory 502 that match one or more search criteria (e.g., one or more user-specified search terms).

In conjunction with touch screen 552, display controller 556, contact module 530, graphics module 532, and text input module 534, the notes module 553 may be used to create and manage notes, to do lists, and the like.

In conjunction with RF circuitry 508, touch screen 552, display system controller 556, contact module 530, graphics module 532, text input module 534, GPS module 535, and browser module 547, the map module 554 may be used to receive, display, modify, and store maps and data associated with maps (e.g., driving directions; data on stores and other points of interest at or near a particular location; and other location-based data).

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 545 may be combined with music player module 546 into a single module (e.g., video and music player module 552). In some embodiments, memory 502 may store a subset of the modules and data structures identified above. Furthermore, memory 502 may store additional modules and data structures not described above.

In some embodiments, device 500 is a device where operation of a predefined set of functions on the device is performed exclusively through a touch screen 552 and/or a touchpad. By using a touch screen and/or a touchpad as the primary input/control device for operation of device 500, the number of physical input/control devices (such as push buttons, dials, and the like) on device 500 may be reduced.

The predefined set of functions that may be performed exclusively through a touch screen and/or a touchpad include navigation between user interfaces. In some embodiments, the touchpad, when touched by the user, navigates device 500 to a main, home, or root menu from any user interface that may be displayed on device 500. In such embodiments, the touchpad may be referred to as a "menu button." In some other embodiments, the menu button may be a physical push button or other physical input/control device instead of a touchpad.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A system comprising:
    a multifunction mobile device, comprising:
        a camera configured to capture multiple frames of a subject;
        a user interface display;
        a processor configured to:
            identify a first frame of the multiple captured frames as a blue frame, wherein the first frame was captured while the subject was illuminated by blue light,
            identify a second frame of the multiple captured frames as a white frame, wherein the second frame was captured while the subject was illuminated by white light;
            associate the blue frame with the white frame,
            detect a feature depicted in the blue frame that is not depicted in the associated white frame,
            indicate the detection of the feature by displaying, on said user interface display: (i) the white frame, and (ii) a graphic indicator overlaid on the displayed white frame at a location corresponding to the location of the detected feature on the associated blue frame, wherein the displaying of the graphic indicator comprises at least one of:
                a) displaying an outline around the feature,
                b) displaying a box surrounding the feature,
                c) displaying an arrow pointing to the feature,
                d) displaying a partially transparent rendition of the detected feature,
                e) displaying any of the graphic indicators of a) to d) in a pulsed manner,
                f) displaying a meter indicating a level of interest for the detected feature.

2. The system of claim 1, wherein the processor is further configured to determine a peak blue level of the captured frames, at a predetermined evaluation frequency.

3. The system of claim 2, wherein the identifying the blue frame and the identifying the white frame comprises synchronizing the identification of the frames with a predefined alternating blue light and white light illumination cycle using a time stamp associated with the captured frames, and a time stamp associated with the peak blue level.

4. The system of claim 1, wherein, responsive to an indication by a user, the blue frame is rendered on a combination of the primary and secondary portions of the display.

5. The system of claim 1, wherein rendering the blue frame separately from the white frame comprises alternately rendering the blue frame and white frame on a common portion of the display.

6. The system of claim 1, further comprising a lamp configured to alternately emit white light and blue light at a predefined illumination cycle, wherein said lamp operates independently of the multifunction mobile device.

7. The system of claim 6, wherein the lamp is mounted with the multifunction mobile device.

8. The system of claim 1, wherein the processor is further configured to store the blue frame in association with the white frame.

9. The system of claim 1, further comprising a polarization difference imaging (PDI) acquisition apparatus configured to acquire a PDI image of the subject, wherein the processor is further configured to detect a PDI feature depicted in the PDI image that is not depicted in any of the blue frame and the white frame and indicate the detection of the PDI feature.

10. A computer program product comprising a non-transitory computer-readable storage medium having program code embodied therewith, the program code executable by at least one hardware processor to:
    identify a first frame of multiple captured frames of a subject as a blue frame, wherein the first frame was captured while the subject was illuminated by blue light;
    identify a second frame of the multiple captured frames of the subject as a white frame, wherein the second frame was captured while the subject was illuminated by white light;
    associate the blue frame with the white frame;
    detect a feature depicted in the blue frame that is not depicted in the associated white frame;
    indicate the detection of the feature by displaying, on a user interface display: (i) the white frame, and (ii) a graphic indicator overlaid on the displayed white frame at a location corresponding to the location of the detected feature on the associated blue frame, wherein the displaying of the graphic indicator comprises at least one of:
        a) displaying an outline around the feature,
        b) displaying a box surrounding the feature,
        c) displaying an arrow pointing to the feature,
        d) displaying a partially transparent rendition of the detected feature,
        e) displaying any of the graphic indicators of a) to d) in a pulsed manner,
        f) displaying a meter indicating a level of interest for the detected feature.

11. The computer program product of claim 10, wherein the identifying the blue frame and the identifying the white frame comprises determining a peak blue level of the captured frames, at a predetermined evaluation frequency.

12. The computer program product of claim 10, wherein the program code is further executable to synchronize the identification of the blue and white frames to a predefined alternating blue light and white light illumination cycle using a time stamp associated with the blue and white frames, and a time stamp of the peak blue level.

13. The computer program product of claim 10, wherein separately rendering comprises simultaneously rendering the white frame on a primary portion of the user interface display and rendering the blue frame on a secondary portion of the user interface display.

14. The computer program product of claim 10, wherein, responsive to an indication by a user, the program code is further executable to render the blue frame on a combination of the primary and secondary portions of the user interface display.

15. The computer program product of claim 10, wherein, responsive to an indication by a user, the program code is further executable to simultaneously render the blue frame on the primary portion of the user interface display and render the white frame on the secondary portion of the user interface display.

16. The computer program product of claim 10, wherein indicating the detection of the feature comprises displaying a graphic indicator overlaid on the rendering of the white frame at a location corresponding to the location of the detected feature on the associated blue frame.

17. The computer program product of claim 10, wherein rendering the blue frame separately from the white frame comprises alternately rendering the blue frames and white frames on a common portion of the display.

18. The computer program product of claim 10, wherein the program code is further executable to store the blue frame in association with the white frame.

19. The computer program product of claim 10, wherein the program code is further executable to receive a polarization difference imaging (PDI) image of the subject, detecting a PDI feature depicted in the PDI image that is not depicted in any of the blue frame and the white frame, and indicating the detection of the PDI feature.

\* \* \* \* \*